United States Patent [19]
Jones

[11] Patent Number: 4,882,439
[45] Date of Patent: Nov. 21, 1989

[54] STEROID INTERMEDIATES

[75] Inventor: David N. Jones, Sheffield, United Kingdom

[73] Assignee: The University of Sheffield, Sheffield, England

[21] Appl. No.: 910,526

[22] Filed: Sep. 19, 1986

[30] Foreign Application Priority Data

Sep. 19, 1985 [GB] United Kingdom ............... 8523184
Jun. 28, 1986 [GB] United Kingdom ............... 8615850

[51] Int. Cl.⁴ ............... C07D 317/12; C07C 49/297; C07C 33/12
[52] U.S. Cl. ............... 549/336; 560/255; 568/327; 568/633; 568/808
[58] Field of Search ............... 549/336; 568/327, 633, 568/763, 808; 560/139, 108, 255

[56] References Cited
U.S. PATENT DOCUMENTS 3,882,106  5/1975  Los ........................ 549/336
3,890,391  6/1975  Eder et al. ................ 568/327
4,064,173 12/1977  Cassal et al. ............. 549/336

Primary Examiner—Nicky Chan
Attorney, Agent, or Firm—Salter & Michaelson

[57] ABSTRACT

Total synthesis of steroids with substitution in the 2,3, 6, 11 or 17 positions comprising the step of cyclization of a compound having the formula

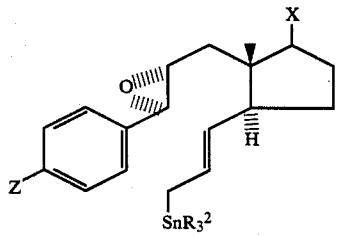 (1)

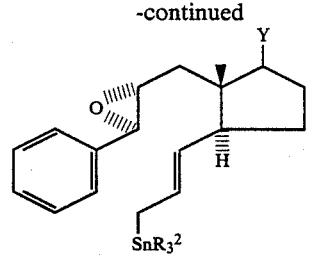

(1A)

or analogues thereof, where X represents =O,

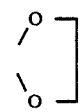

or β-substituted

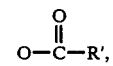

Y represents =O, β-oriented

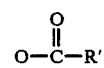

or β-orientated OH, R' and R² may be the same or different and R' represents alkyl or aryl and R² represents alkyl and Z represents ether or hindered ester to form the novel compounds

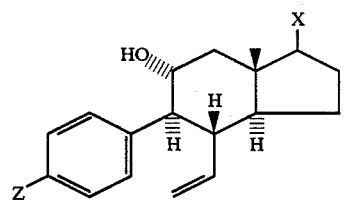 (2)

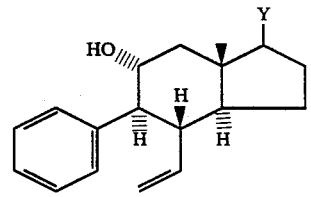

(2A)

1 Claim, No Drawings

STEROID INTERMEDIATES

This invention relates to total steroid synthesis and to novel intermediates in said synthesis.

Steroid derivatives find widespread use pharmaceutically for example in the control of inflammation, in the treatment of certain types of cancer, and in hormone replacement therapy. The control of human fertility by administration of steroids has also established for such compounds a position of commercial significance.

Many of these steroids are prepared by chemical transformation of estrone. Estrone itself is manufactured commercially from compounds extracted from plant sources for example diosgenin extracted from Mexican yams and stigmasterol extracted from soybeans. It is envisaged that the availability of plant sources for the manufacture of estrone may decline. Although methods for total synthesis of estrone have been proposed they seem commercially unattractive when compared to the semi-synthetic methods using plant sources.

Steroids with unusual substitution patterns are less readily accessible from estrone. Amongst the most important locations for unusual substitution are the 6 and 11 positions. The presence of a 6-substituent has the effect of markedly increasing the physiological potency of some therapeutically important steroids whilst the presence of an 11-substituent is normally essential for the activity of anit-inflammatory steroids. In addition steroids with an oxygen function at the 3-position are pharmacologically much more interesting than 3 unsubstituted compounds.

At present there is no direct chemical method available for the introduction of functionality at the 11 position into the pre-existing steroid skeleton. Microbiological processes are used for this purpose.

A commercially acceptable total synthesis of steroids with substitution at the 11-position, and of steroids with substitution in both 6 and 11 positions and with subsitution in the 3, 6, and 11 positions is, therefore, of considerable interest.

According to the invention there is provided a total synthesis of steroids with 11 position substitution and of steroids with 6 and 11 position substitution characterized by the steps of cyclization of a compound having the formula

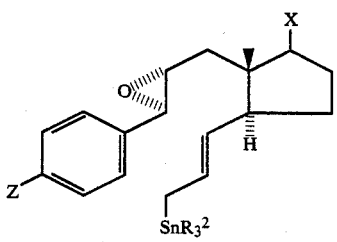

where X represents =O,

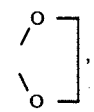

or Beta orientated

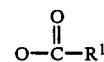

and $R^1$ and $R^2$ may be the same or different and $R^1$ represents alkyl and $R^2$ represents alkyl and Z represents alkoxy to form a compound having the formula

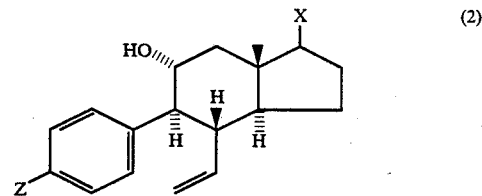

Further, according to the invention there is provided a total synthesis of steroids with 11 position substitution and of steroids with 6 and 11 position substitution characterized by the steps of cyclization of a compound having the formula

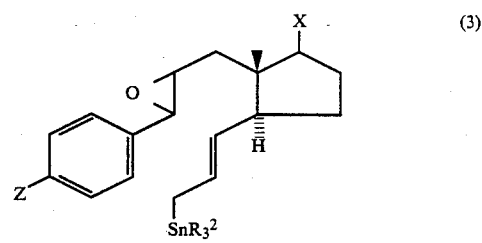

where X represents =O,

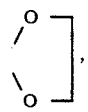

or Beta orientated

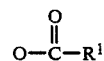

and $R^1$ and $R^2$ may be the same or different and $R^1$ represents alkyl and $R^2$ represents alkyl and Z represents alkoxy to form a compound having the formula

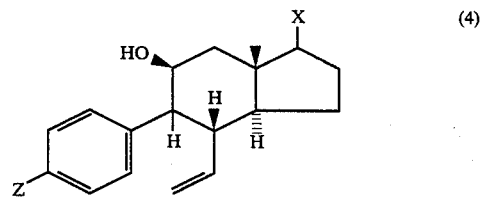

Similarly, according to the invention there is provided a total synthesis of steroids with 11 position substitution and of steroids with 6 and 11 position substitution and of steroids with 2, 6 and 11 position substitution characterized by the steps of cyclization of a compound having the formula

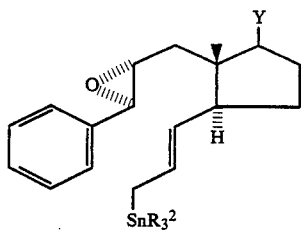 (1A)

where Y represents =O,

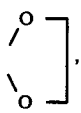,

β-orientated

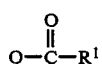

or β-orientated OH and R¹ and R² may be the same or different and R1 represents alkyl and R² represents alkyl to form a compound having the formula

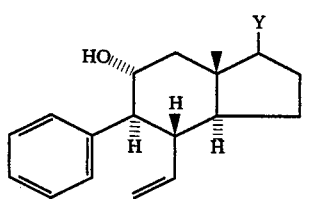 (2A)

According to the invention there is also provided a total synthesis of steroids with 11 position substitution and of steroids with 6 and 11 position substitution and of steroids with 2, 11, and 17 substitution characterized by the steps of cyclization of a compound having the formula

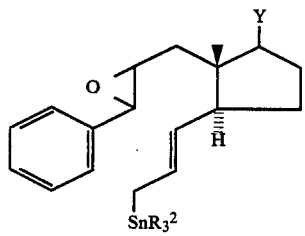 (3A)

where Y represents Beta orientated OH or Beta orientated

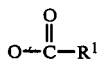

and R¹ and R² may be the same or different and R¹ represents alkyl and R² represents alkyl to form a compound having the formula

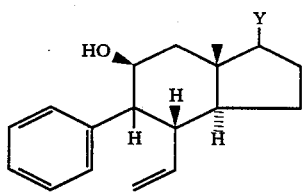 (4A)

The products (2) and (4) of the cyclization process as defined above can, in a relatively few steps as will be explained hereinafter, be converted into steroids with a functional group at the 11-position, and to steroids with functional groups at both 6 and 11 positions and more particularly at the 3, 11, and 17 positions and at the 3, 6, 11, and 17 positions for example having the formulae

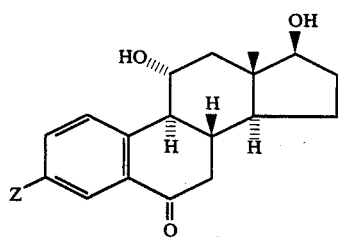 (5)

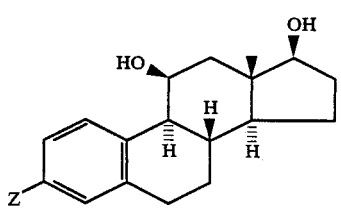 (6)

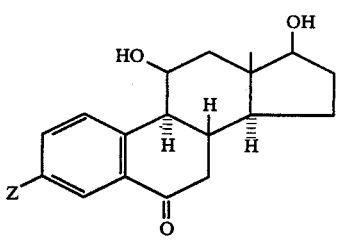 (6A)

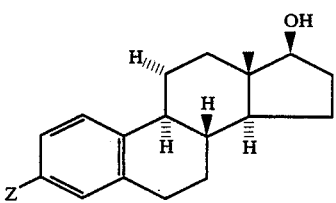 (6B)

The products (2A) and (4A) of the cyclization process as defined above can also, in a relatively few steps, be converted into steroids with a functional group at the 11-position, and to steroids with functional groups at both 6 and 11 positions and more particularly at the 2, 11, and 17-positions for example having the formulae

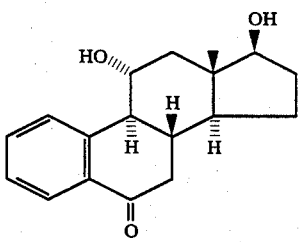     (5A)

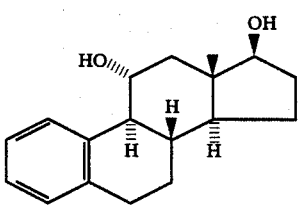     (6C)

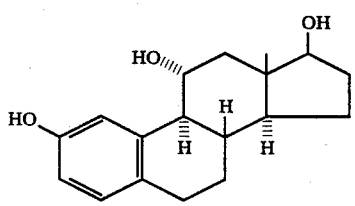     (6D)

Such steroids are of pharmacological interest and moreover occupy a key position in schemes for producing a wide variety of functionalized steroids by known methods. For example the functional groups of the 6 and 11 positions have different reactivities which can be manipulated chemically for selective removal thereof and introduction if desired of additional groups at the 7, 9, 12, and/or 16 positions.

In addition to utilization as intermediates for the production of 11-functionalized steroids and of 6, 11-difunctionalized steroids and of 2,11-difunctionalized steroids the products (2) and (4) and (2A) and (4A) of the cyclization process are novel compounds of pharmacological interest. Moreover the said products (2) and (4) and (2A) and (4A) can be transformed into derivatives also having pharmacological properties.

The invention therefore, also provides novel compounds having the formulae

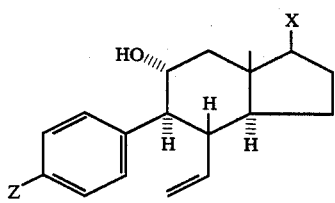     (2)

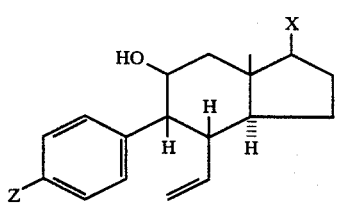     (4)

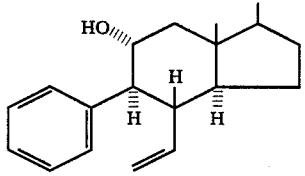     (2A)

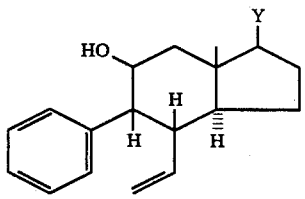     (4A)

where X and Y and Z are as previously defined.

The starting compounds (1) and (3) for the cyclization process can be prepared by any suitable route. We have found, and it is a preferred embodiment of the invention that compounds (1) and (3) can be conveniently prepared by the following synthesis.

Step 1-The anion of an allyl sulphone for example allyl phenyl sulphone

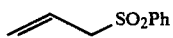

generated for example by treatment with n-butyl lithium in a mixture of tetrahydrofuran and hexamethylphosphoric triamide, is treated at −78° C. with an enone, for example 2-methylcyclopentenone.

The lithium enolate so formed is trapped by addition of the reaction mixture to an allylic halide, for example 3-methoxycinnamyl bromide to form the compound

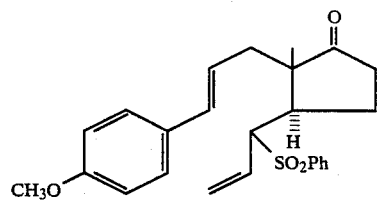     (7)

In variations of this procedure the lithium enolate may be treated with triphenyltin chloride to give the tin enolate, which is then allowed to react with 4-methoxycinnamyl bromide to give compound (7), or the lithium enolate is treated with trimethylsilyl chloride to give the trimethylsilyl enol ether, which is isolated and then allowed to react with 4-methoxy-1-(1-hydroxypropenyl)benzene with zinc bromide catalysis to give the compound (7).

In this first step all the carbon atoms of the steroid skeleton are introduced, and only one diastereoisomer of the product is obtained. The reaction therefore proceeds stereoselectively to give the required trans junction about C-13–C-14, and, stereoselectively to give one epimer at C-8. Moreover by appropriate choice of starting materials functionality can be optionally introduced into the 2 position, or omitted from the 3 position, and different alkyl groups can be introduced into the C-13 position. For example the allylic halide can be one selected from compounds having the formula

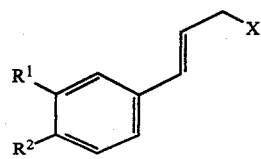

where R¹ and R² is H, and where R¹ is H and R² is oxyalkyl, and where R¹ and R² is oxyalkyl, and X is halide or sulphonate ester and the enone can be selected from compounds having the formula

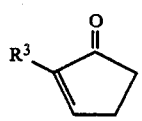

where R³ is alkyl.

The allyl sulphone that can be used includes compounds having the formula

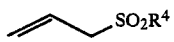

where R⁴ represents phenyl, p-tolyl, t-butyl, 2-pyridyl, 2-(N-methylimidazolyl) or 2-thiazolinyl. In addition allyl alkyl sulphones, particularly those in which the alkyl group is chiral, can also be used. The latter sulphones provide a useful basis for enantioselective preparation of analogues of compound 7. The advantages of the use of an allyl sulphone in the above process can be appreciated when the Step 1 described above is compared with an analogous process in which an allyl sulphide is employed. When an allyl sulphide is used an oxidation step is required before proceeding to reduction to produce the 17β-alcohol (see subsequent Step 2). An equivalent oxidation step is not required when an allyl sulphone is used and potential difficulties relating to that selective oxidation are thus avoided. A most important advantage of the use of an allyl sulphone in this step is that only one diastereoisomer at C-8 is formed. Wtih an allyl sulphide a mixture of diastereoisomers at C-8 is obtained, which complicates isolation and characterization procedures.

Step 2-The product of step 1 is reduced preferably using a hydride for example sodium borohydride in methanol and the 17β alcohol obtained.

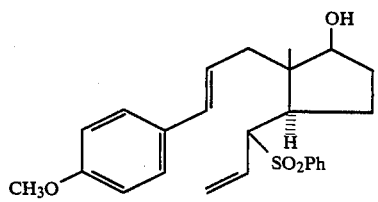

Step 3-The 17β alcohol produced in step 2 is converted into an ester by treatment with for example trimethylacetyl chloride

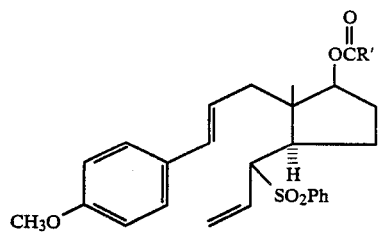

Acetyl chloride can be used as an alternative to trimethylacetyl chloride, but the acetate leads to lower yields in the subsequent steps 4 and 5.

Step 4-A mixture of the 9α,11α epoxide (10) and 9β,11β-epoxide (11) is produced by oxidation of the product of Step 3 using for example a peroxyacid such as m-chloroperbenzoic acid in the presence of anhydrous potassium fluoride in dichloromethane at room temperature

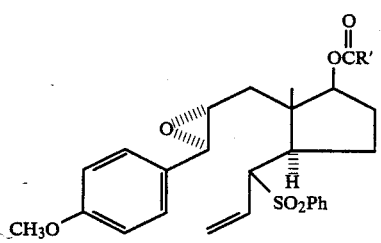

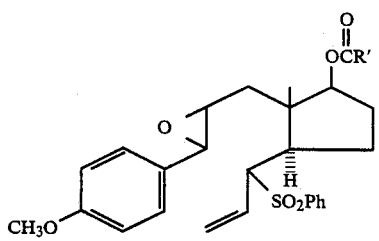

The ratio of (10B) to (11B) formed when the reaction is performed at room temperature is ca. 2:1, whereas at 0° C. the ratio is 3.3:1. The mixture of epoxides in the present process may decompose on chromatography on silica and that mixture is, therefore, used in the next step without purification.

The compounds (10) and (11) may be converted into the same steroids with 'correct' stereochemistry so that the absence of high stereoselectivity in step 4 is not serious. Compound (11) can be used to obtain steroids of unnatural configuration at position 9.

Step 5-The mixture of epoxides from Step 4 is reacted with an alkyl tin hydride which would not reduce the epoxy group for example tri-n-butyltin hydride to yield the starting materials for the cyclization process

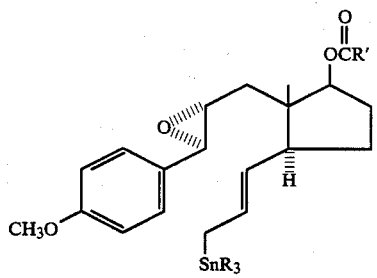

(1) R' = Me
(1B) R' = Bu$^t$

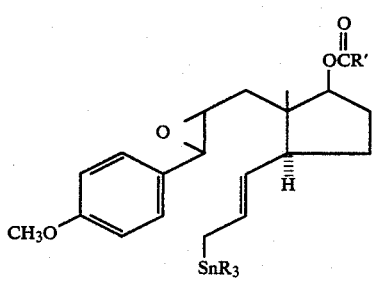

(3) R' = Me
(3B) R' = Bu$^t$

For the 9α,11α epoxide (1) the cyclization process of the invention proceeds to give compound (2) at an appreciable rate under the reaction conditions of Step 5. The cyclization may be further promoted by a variety of proton acids or Lewis acids for example trifluoroacetic acids or tin(IV) chloride or zinc bromide, preferably at reduced temperature for example at from −78° C. to 0° C. For the 9β,11β epoxide (3) the cyclization process of the invention to give (4) can be promoted by a variety of Lewis acids for example tin(IV) chloride or zinc bromide. The process is preferably carried out at reduced temperature for example at from −78° C. to 0° C.

The starting compounds (1A) and (3A) for the cyclization process can also be prepared by any suitable route. We have found, and it is a preferred embodiment of the invention that compounds (1A) and (3A) can be conveniently prepared from cinnamyl bromide by procedures analogous to those in the foregoing steps 1-5, which provide in sequence the compounds (7A), (8A), (9A), and (10A) and (11A), and ultimately (1A) and (3A). For the conversion of (9A) into the epoxides (10A) and (11A) metachloroperbenzoic acid was used. It was not necessary to add potassium fluoride. The epoxides (10A) and (11A) were chromatographically identical and could not be separated, but they did not decompose on chromatography.

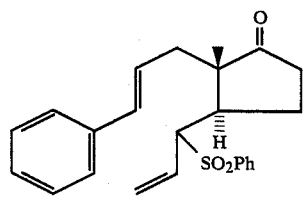

(7A)

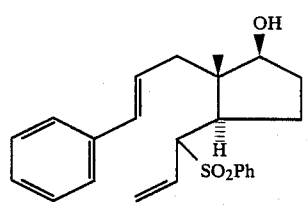

(8A)

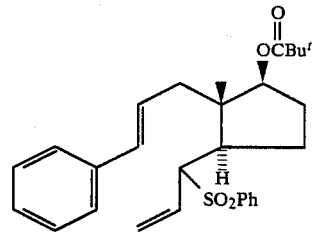

(9A)

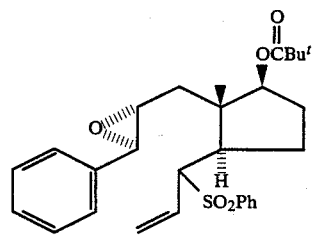

(10A)

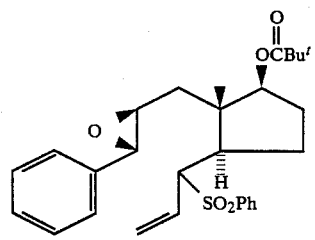

(11A)

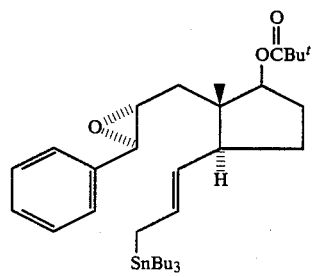

(1A)

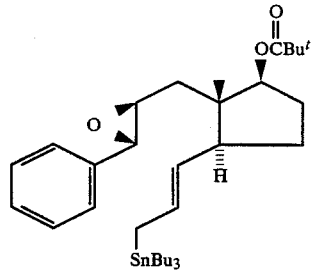

(3A)

As previously mentioned the novel compounds produced by the cyclization process of the invention can be converted into 11-functionalized steroids and 6,11-functionalized steroids. Preferred synthesis for those conversions are as follows. (The step numbers that follow assume that Step 6 in a complete synthesis to the steroids would be the cyclization process of the invention).

FIRST SYNTHESIS

Step 7-The product (2) (X=17B-OAc) (Z=OMe) of the cyclization process is hydrolysed to the 3-methoxy 11α,17β-diol

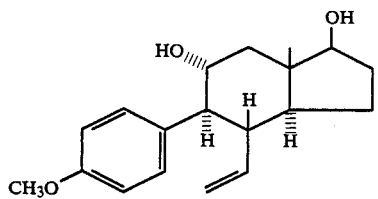

(12)

Step 8-The diol from Step 7 is esterified to give the 3-methoxy-11α,17β-di(trimethylacetate)

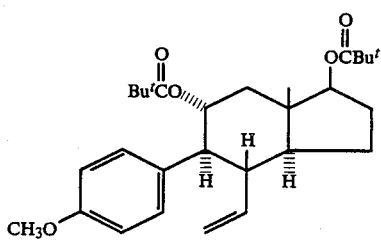

(13)

The methoxy diester (13) is also obtained by esterification with trimethylacetyl chloride of the product (2) X=17β-trimethylacetoxy) of the cyclization process.

Step 9-The product from Step 8 is converted into the corresponding 6-alcohol by hydroboration followed by oxidation

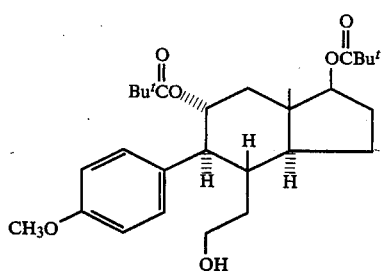

(14)

Step 10-The 6-hydroxy compound formed in Step 9 is further oxidised to give the acid

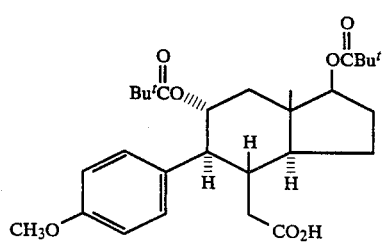

(15)

Step 11-The acid from Step 10 is converted into the acid chloride and then treated with aluminium chloride to produce the 3-methoxy-11α,17β-di(trimethylacetoxy)-6-keto steroid

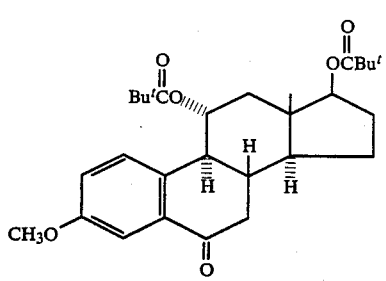

(16)

Step 12-Hydrolysis of the fully cyclized product from Step 11 furnishes the 3-methoxy-11α,17β-dihydorxy-6-keto-estra-1,3,5(10)-triene

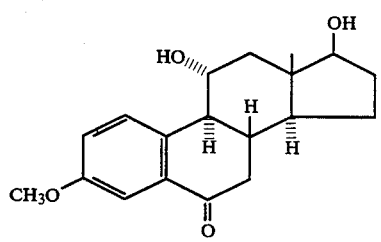

(5)

SECOND SYNTHESIS

Step 7a-The product (4) (X=OAc) (Z=Ome) of the cyclization process is oxidised to the corresponding 11-ketone

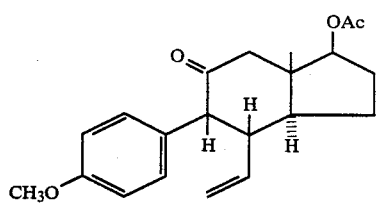

(17)

Step 8a-Under basic conditions the ketone obtained in Step 7a is converted into its isomer at C-9.

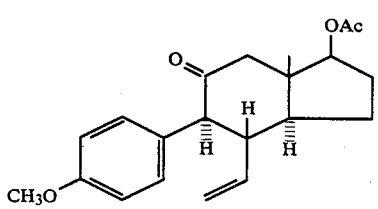

(18)

Step 9a-The ketone obtained in Step 8a is reduced preferably using a hydride for example sodium borohydride and the 11β-alcohol obtained, (together with a small proportion of the 11α alcohol)

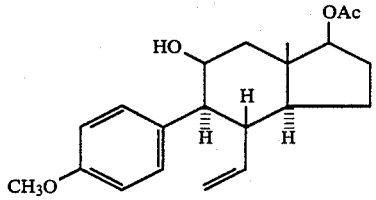

(19)

Step 10a-The 11β-alcohol obtained in Step 9a is esterified by treatment for example with acetyl chloride to give the 3-methoxy-11β,17β-diacetoxy derivative

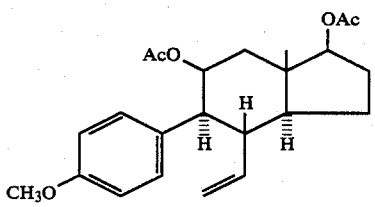

(20)

Step 11a-The methoxy diacetate from Step 10a is converted into the corresponding 6-alcohol by hydroboration followed by oxidation

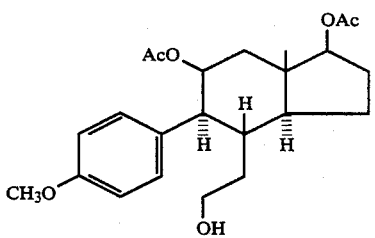

(21)

Step 12a-Oxidation of the 6-alcohol from Step 11a gives the corresponding acid

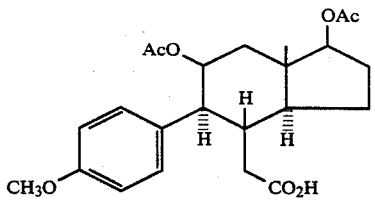

(22)

Step 13a-The acid from Step 12a is converted into the acid chloride and then treated with aluminium chloride to produce the 3-methoxy-11β,17β-diacetoxy-6-keto steroid

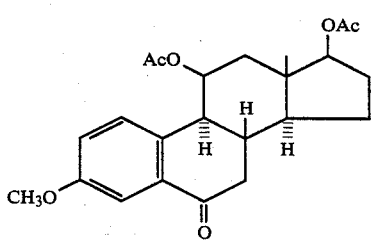

(23)

Step 14a-Hydrolysis of the fully cyclized product from Step 13a furnishes the 3-methoxy-11β,17β-dihydroxy-6-keto-estra-1,3,5(10)-triene

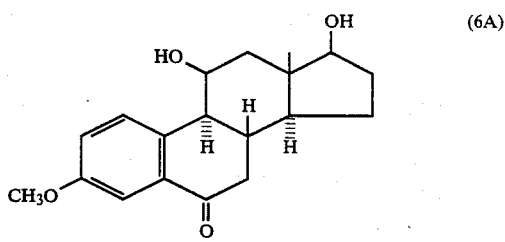

(6A)

THIRD SYNTHESIS

3-Methoxy-11β,17β-diacetoxy-6-hydroxy-5,6-seco-estra-1,3,5(10)-triene (21) is obtained by Step 11a as before Step 12b-The 6-hydroxy compound from Step 11a is converted into the corresponding chloride by treatment for example with triphenyl phosphine in carbon tetrachloride

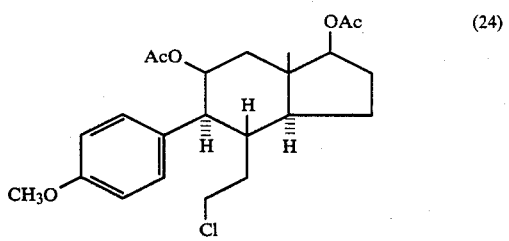

(24)

Step 13b-The chloride from Step 12b is treated with aluminium chloride to give the 3-methoxy-11β,17β-diacetoxy steroid

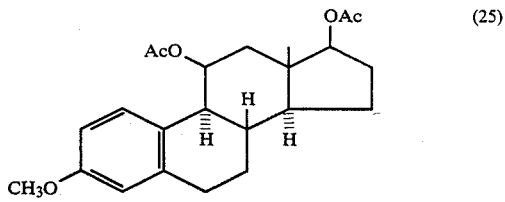

(25)

Step 14b-Hydrolysis of the fully cyclized product from Step 13b furnishes the 3-methoxy-11β,17β-dihydroxy-estra-1,3,5(10)-triene

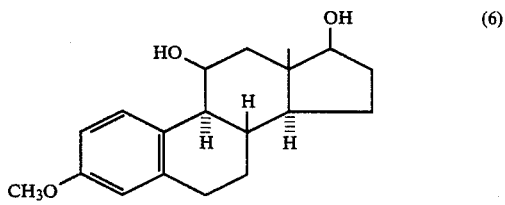

(6)

FOURTH SYNTHESIS

3-Methoxy-11α,17β-di(trimethylacetoxy)-6-hydroxy-5,6-seco-estra-1,3,5(10)-triene (14) is obtained by step 9 as before.

Step 10c-The 6-hydroxy compound from Step 9 is converted into the corresponding methanesulphonate by treatment with methanesulphonyl chloride and triethylamine, and the crude product is treated with aluminium chloride in dichloromethane to give the 3-methoxy-11α,17β-di(trimethylacetoxy) steroid

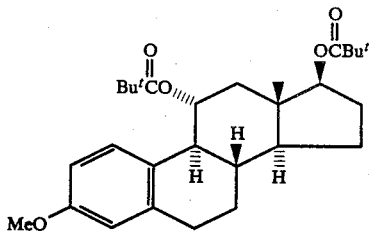
(26)

Step 11c-The fully cyclized product from Step 10c is treated with lithium aluminium hydride to give 3-methoxy-11α,17β-dihydroxy-estra-1,3,5(10)-triene

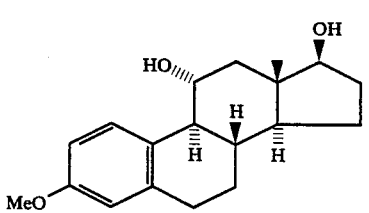
(6B)

FIFTH SYNTHESIS

Methods analogous to the foregoing first synthesis are used to convert the product of cyclization (2A) (Y=17β-trimethylacetoxy) into 11α,17β-6-keto-estra-1,3,5(10)-triene (5A) via the intermediates (13A), (14A), (15A), and (16A).

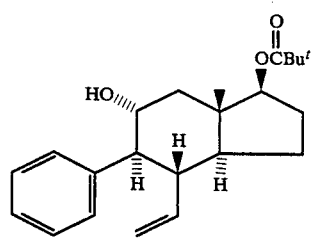
(2A)

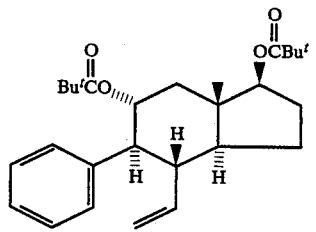
(13A)

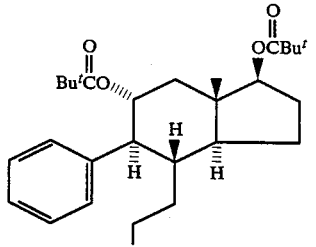
(14A)

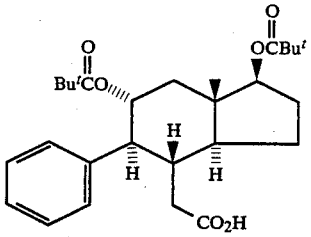
(15A)

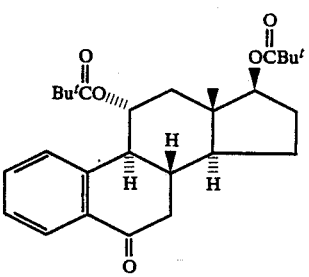
(16A)

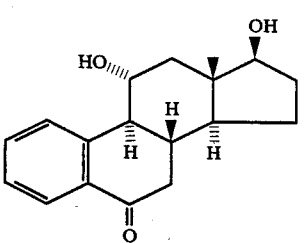
(5A)

SIXTH SYNTHESIS

The hydroxy di(trimethylacetate) (14A) is obtained by the first two steps of the foregoing fifth synthesis. This is converted by steps analogous to the fourth synthesis via the diester (26A) into 11α,17β-dihydroxy-estra-1,3,5(10)-triene (6C).

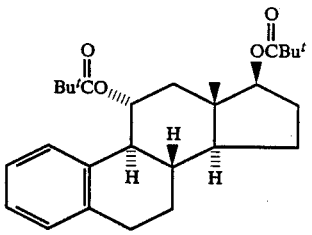
(26A)

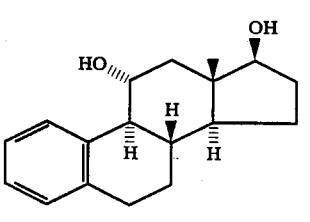
(6C)

SEVENTH SYNTHESIS

11α,17β-Di(trimethylacetoxy)-estra-1,3,5(10)-triene (26A) was obtained as before (see sixth synthesis).

Step 11d-The diester (26A) is treated with acetyl chloride and aluminium chloride to give the corresponding 2-acetyl compound

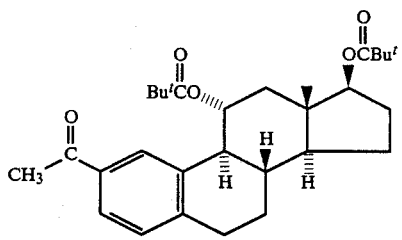

Step 12d-The product of Step 11d is treated with metachloroperbenzoic acid to give the 2-acetoxy compound

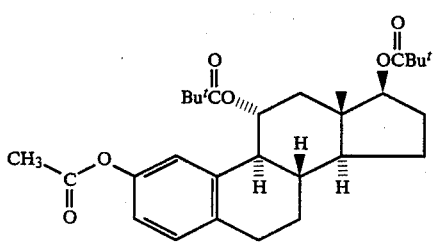

Step 13d-The triester (28) is treated with lithium aluminium hydride to give 2,11α,17β-trihydroxyestra-1,3,5(10)-triene

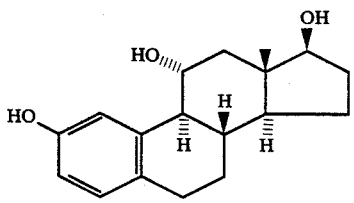

In the foregoing description, the production of compounds 1, 2, 3, and 4 and the production of compounds derived therefrom has been exemplified by compounds with a methoxy group in the 3-position. It is to be understood that the substitution in the 3-position may be a different ether or a hindered ester group for example RO— where R is alkyl, and ArCH$_2$O— or Ar$_2$CHO— where Ar is phenyl or tolyl or 4-methoxyphenyl or other alkyl- or alkoxy-substituted phenyl residues, and RC(O)O— where R is t-butyl or 1-adamantyl or 2,6-dialkylphenyl or 2,4,6-trialkylphenyl.

EXPERIMENTAL

Melting points were determined with a Kofler block apparatus. Infra-red spectra were determined with a Perkin-Elmer 157G spectrophotometer, and mass spectra with a Kratos MS25 or MS80 spectrometer. Proton n.m.r. spectra refer to deuteriochloroform solutions with tetramethylsilane as internal standard: they were determined at 220 MHz (unless otherwise indicated), with a Perkin-Elmer R34 spectrometer, and spectra at 250 and 400 MHz were determined respectively with Bruker AM250 and WH400 instruments. Column chromatography was performed with Merck 7736 60H silica gel. Ether refers to diethyl ether, and light petroleum to the fraction boiling between 40° and 60° C. After extraction procedures, organic solvents (usually ether) were dried over magnesium sulphate. In the nomenclature of the following compounds steroid numbering is used.

3-Methoxy-8ξ-phenylsulphonyl-8,9-seco-5,6-secoestra-1,3,5(10),6,9(11)-pentaene-17-one (7).

Method 1.

A solution of allyl phenyl sulphone (0.379 g, 2.1 mmol) in dry tetrahydrofuran (THF) (6ml) and hexamethylphosphoric acid triamide (HMPA) (0.8 ml) was treated with n-butyl-lithium (0.91 ml of a 2.3M solution in hexane, 2.1 mmol) at −78° C. under argon. After 15 min the deep orange solution was treated with 2-methylcyclopentenone (2) (0.2 g, 2.1 mmol), the mixture was stirred for a further 15 min, and then transferred by cannula dropwise to a solution of 4-methoxycinnamyl bromide (1.2 g, 5.3 mmol) in dry THF (6 ml) at −20° C. After a further 30 min at −20° C. a solution of thiourea (0.8 g, 10.5 mmol) in dimethylformamide (10 ml) was added, and the mixture was heated at 100° C. for 10 min, and the solvent was then removed by evaporation under reduced pressure. The residue was treated with water (10 ml) and extracted with ether (3×20 ml). After the ethereal extract was washed with water, dried, and evaporated, the residue was chromatographed on silica (10 g) and eluted with ether-light petroleum (2:3) to give the product (7) (660 mg, 75%), m.p. 135–6° C. (from ethanol), $\nu_{max}$ 1735 (CO), 1140 cm$^{-1}$ (SO$_2$), δ (250 MHz) 7.7–7.4 (7 H, m, aromatic protons), 6.87 (2 H, d, J 8 Hz, 2- and 4-protons), 6.49 (1 H, d, J 16 Hz, ArCH), 6.04 (1 H, dt, J 16 and 8 Hz, ArC=CH), 5.87 (1H, dt, 17 and 10 Hz, 7-proton), 5.23 (1 H, dd, H 10 and 1 Hz, cis 6-proton), 4.81 (1 H, dd, J 17 and 1 Hz, trans 6-proton), 3.83 (3 H, s, OCH$_3$), 3.80 (1 H, dd, J 10 and 2 Hz, 8-proton), 3.22 (1 H, ddd, J 10, 5.5, and 2 Hz, 14-proton), 2.5–1.9 (6 H, m), 0.91 (3 H, s, 18—CH$_3$); (Found: C, 70.5; H, 6.5; S, 7.5; M+ 424.1712. C$_{25}$H$_{28}$O$_4$S requires C, 70.8; H, 6.6; S, 7.6%; M 424.1708).

Method 2.

A solution of allyl phenyl sulphone (0.632 g, 3.5 mmol) in dry tetrahydrofuran (THF) (10 ml) and hexamethylphosphoric acid triamide (HMPA) (1.33 ml) was treated with n-butyl-lithium (2.3 ml of a 1.5M solution in hexane, 3.5 mmol) at −78° C. under argon. After 15 min the deep orange solution was treated with 2-methylcyclopentenone (2) (0.333 g, 3.5 mmol), the mixture was stirred for a further 15 min, and then treated with triphenyltin chloride (1.47 g, 382 mmol). After being stirred for 30 min, the mixture was treated with a solution of 4-methoxycinnamyl bromide (2.36 g, 10.4 mmol) in dry THF (12 ml), and allowed to warm to room temperature. After a further three hours a 10% solution of potassium fluoride was added, the mixture was stirred for 15 min, filtered, and the filtrate evaporated to dryness. The residue was extracted with ether, and the ethereal extract was processed in the same way as described in Method 1 to give the product (7) (617 mg, 42%).

Method 3.

A solution of allyl phenyl sulphone (2.767 g) in dry tetrahydrofuran (THF) (29 ml) and hexamethylphosphoric acid triamide (HMPA) (5.4 ml) was treated with n-butyl-lithium (11.97 ml of a 1.5M solution in hexane) at −78° C. under argon. After 15 min the deep orange solution was treated with 2-methylcyclopentenone (2) (1.459 g), the mixture was stirred for a further 15 min, and then treated with chlorotrimethylsilane (19.1 ml). After evaporation of the solvent under reduced pressure the residue was extracted with petroleum ether containing a few drops of triethylamine, and the extract washed rapidly with water and dried (MgSO4). Evaporation of the solvent gave the crude enol silyl ether (3.90 g, 81%), a portion of which (200 mg, 0.63 mmol) was dissolved in dry acetonitrile (0.5 ml) and treated with anhydrous zinc bromide (28 mg, 0.12 mmol). After 15 min a solution of 4-methoxy-1-(1-hydroxyprop-3-enyl)-benzene (103 mg, 0.63 mmol) in dry acetonitrile (0.5 ml) was added, and the resulting solution was kept at 40° C. for 40 hours. The solution was cooled, water (5 ml) was added, and the mixture was extracted with dichloromethane. The extract was dried and evaporated to give a residue which was chromatographed on silica eluted with ether-light petroluem (3:10) to give the product (7) (119 mg, 45%)

8ξ-phenylsulphonyl-8,9-seco-5,6-secoestra-1,3,5(10),6,9(11)-pentaene-17-one (7A).

This was prepared by Method 1 (outlined above) from cinnamyl bromide (4.44 g) and 2-methylcyclopentenone (1.45 g) which gave the product (7A) (3.887 g, 64%), m.p. 79–81° C., $\nu_{max}$ 1740 (CO), δ (250 MHz) 7.9–7.2 (10 H, m, aromatic protons), 6.56 (1 H, d, J 16 Hz, 9-proton), 6.20 (1 H, dt, J 16 and 8 Hz, 11-proton), 5.87 (1 H, dt, 16.5 and 10 Hz, 7-proton), 5.23 (1 H, dd, H 10 and 1 Hz, cis 6-proton), 4.80 (1 H, dd, J 16.5 and 1 Hz, trans 6-proton), 3.80 (1 H, dd, J 10.5 and 2 Hz, 8-proton), 3.22 (1 H, ddd, J 10.5, 5.5, and 2 Hz, 14-proton), 2.5–1.9 (6 H, m), 0.92 (3 H, s, 18-CH3);

(Found: C, 72.85; H, 6.95; S, 8.4; M+ 394. $C_{24}H_{26}O_3S$ requires C, 73.1; H, 6.9; S, 8.1%; M 394).

3-Methoxy-8ξ-phenylsulphonyl-8,9-seco-5,6-secoestra-1,3,5(10),6,9(11)-pentaene-17-ethylene ketal (7E).

A solution of the keto sulphone (7) (197 mg, 0.46 mmol) and p-toluenesulphonic acid (10 mg) in a mixture of benzene (30 ml) and ethane-1,2-diol (86 mg, 1.4 mmole) was refluxed for 6 hours, with separation of water by means of a Dean-Stark apparatus. The cooled solution was passed through a column of alumina (2 g) and evaporated to give the product (7E) (133 mg, 61%) as an oil, $\nu_{max}$ 1150 cm$^{-1}$ (SO2), δ 7.63–7.28 (7 H, m, aromatic protons), 6.87 (2 H, d, J 8.5 Hz, 2- and 4-protons), 6.44 (1 H, d, J 15.5 Hz, 9-protons), 6.17 (1 H, ddd, J 15.5, 8, and 6.5 Hz, 11-proton), 5.90 (1 H, dt, J 17 and 10 Hz, 7-proton), 5.19 (1 H, dd, J 10 and 1 Hz, cis-6-proton), 4.71 (1 H, dd, J 17 and 1 Hz, trans-6-proton), 3.98–3.80 (5 H, m, OCH2CH2O and 8-proton), 3.83 (3 H, s, OCH3), 3.13 (1 H, t, J 10 Hz, 14-proton), 2.44–1.77 (6 H, m), 0.94 (3 H, s, 18-CH3), (Found: M+ 468.1943. $C_{27}H_{32}O_5S$ requires 468.1970).

3-Methoxy-8ξ-phenylsulphonyl-8,9-seco-5,6-secoestra-1,3,5(10),6,9(11)-pentaene-17β-ol (8).

Sodium borohydride (1.37 g, 36 mmol) was added to a solution of the oxo-sulphone (7) (3.05 g, 7.2 mmol) in dry ethanol (130 ml) at 20° C. After 90 min dilute hydrochloric acid was added, the solvent was evaporated under reduced pressure, and the residue was partitioned between ether and water. The ethereal extract was washed with dilute hydrochloric acid and water, dried and evaporated to give a residue which was chromatographed on silica (30 g). Elution with ether-light petroleum (1:1) gave the product (8) (2.97 g, 97%), m.p. 45°–6° C., $\nu_{max}$ 3520 (OH) and 1140 cm$^2$ (SO2), δ (250 MHz) 7.52–7.3 (7 H, m, aromatic protons), 6.86 (2 H, d, J 8 Hz, OCH3), 6.47 (1 H, d, J 15 Hz, 9-proton), 6.41 (1 H, dt, J 15 and 8 Hz, 11-proton), 5.88 (1 H, dt, J 16.5 and 10 Hz, 7-proton), 5.23 (1 H, dd, H 10 and 1 Hz, cis 6-proton), 4.81 (1 H, dd, J 16.5 and 1 Hz, trans 6-proton), 3.90 (1 H, t, J 8 Hz, 17-proton), 3.82 (3 H, s, OCH3), 3.81 (1 H, dd, J 10 and 1.5 Hz, 8-proton), 2.70 (1 H, dt, J 10 and 1.5 Hz, 14-proton), 2.28 (2 H, ddd, J 8, 5, and 1 Hz, 12-protons), 2.06 (1 H, m, 16-proton), 1.95 (2 H, m), 1.70 (1 H, br s, OH), 1.52 (1 H, m, 16-proton), 0.79 (3 H, s, 18-CH3);

(Found: C, 70.4; H, 6.9; S, 7.7%; M+ 426.1871. $C_{25}H_{30}O_4S$ requires C, 70.4; H, 7.0; S, 7.5%; M 426.1864).

3-Methoxy-8ξ-phenylsulphonyl-8,9-seco-5,6-secoestra-1,3,5(10),6,9(11)-pentaene-17β-yl acetate (9).

A solution of the hydroxy-sulphone (8) (1.52 g, 3.57 mmol) in dry benzene (20 ml) was treated with dry silver cyanide (956 mg, 7.14 mmol) and acetyl chloride (1.3 ml, 18.2 mmol) at room temperature. After 16 h ether (20 ml) was added, the solution was filtered through Hyflosupercel, and the filtrate evaporated under reduced pressure. Chromatography of the residue on silica (20 g) eluted with ether-light petroleum (1:1) gave the product (9) (1.60 g, 96%), m.p. 118°–119° C. (from ether-light petroleum), $\nu_{max}$ 1730 cm$^{-1}$ (CO), δ 7.72–7.26 (7 H, m, aromatic protons), 6.86 (2 H, d, J 8 Hz, 2- and 4-protons), 6.40 (2 H, d, J 16 Hz, 9-proton), 6.11 (1 H, dt, J 16 and 8 Hz, 11-proton), 5.89 (1 H, dt, J 17 and 10 Hz, 7-proton), 5.27 (1 H, dd, J 10 and 1 Hz, cis 6-proton), 4.87 (1 H, dd, J 8 and 6 Hz, 17-proton), 4.86 (1 H, dd, J 17 and 1 Hz, trans 6-proton), 3.82 (3 H, s, OCH3), 3.80 (1 H, dd, J 10 and 2 Hz, 8-proton), 2.69 (1 H, ddd, J 10, 8, and 2 Hz, 14-proton), 2.26–1.87 (4 H, m, 15- and 16-protons), 1.98 (3 H, s, COCH3), 0.84 (3 H, s, 18-CH3);

(Found: C, 69.3; H, 6.8; S, 6.7%; M+ 468.1967. $C_{27}H_{32}O_5S$ requires C, 69.2; H, 6.8; S, 6.8%; M 468.1970).

8ξ-Phenylsulphonyl-8,9-seco-5,6-secoestra-1,3,5(10),6,9(11)-pentaene-17β-yl trimethylacetate (9A).

Treatment of the alcohol (8A) (3.50 g) with trimethylacetyl chloride and silver cyanide in the above manner gave the ester (9A) (3.35 g, 79%), as a waxy solid, $\nu_{max}$ 1720 (C=O) and 1145 cm$^{-1}$ (SO2), δ 7.72–7.18 (10 H, m, aromatic protons), 6.44 (1 H, d, J 16 Hz, 9-proton), 6.25 (1 H, dt, J 16 and 7 Hz, 11-proton), 5.88 (1 H, dt, J 17 and 10 Hz, 7-proton), 5.25 (1 H, dd, J 10 and 1 Hz, cis 6-proton), 4.83 (1 H, dd, J 17 and 1 Hz, trans 6-proton), 4.85 (1 H, dt, J 8 and 1.5 Hz, 17-proton), 3.79 (1 H, dd, J 10 and 1.5 Hz, 8-proton), 2.73 (1 H, dt, J 10 and 1.5 Hz, 14-proton), 2.29–1.35 (6 H, m), 1.13 (9 H, s, OBu$^t$), 0.86 (3 H, s, 18-CH3), (Found: C, 72.6; H, 7.7; S, 6.9; M+ 480. $C_{29}H_{36}O_4S$ requires C, 72.5; H, 7.55; S, 6.7%; M 480).

3-Methoxy-8ξ-phenylsulphonyl-8,9-seco-5,6-secoestra-1,3,5(10),6,9(11)-pentaene-17β-yl trimethylacetate (9B).

A solution of the hydroxy-sulphone (8) (201 mg, 0.94 mmol) in dry benzene (2 ml) was treated with dry silver cyanide (130 mg, 0.94 mmol) and trimethylacetyl chloride (74 mg, 0.61 mmol) at room temperature. After 19 h ether (2 ml) was added, the solution was filtered through Hyflosupercel, and the filtrate evaporated under reduced pressure. Chromatography of the residue on alumina eluted with ethyl acetate-light petroleum (1:10) gave the product (9B) (162 mg, 61%), m.p. 115°–116° C. (from ether-light petroleum), $\nu_{max}$ 1730 cm$^{-1}$ (CO), δ 7.72–7.27 (7 H, m, aromatic protons), 6.86 (2 H, d, J 8 Hz, 2- and 4-protons), 6.39 (1 H, d, J 15.5 Hz, 9-proton), 6.10 (1 H, dt, J 15.5 and 8 Hz, 11-proton), 5.89 (1 H, dt, J 17 and 10 Hz, 7-proton), 5.26 (1 H, dd, J 10 and 1 Hz, cis 6-proton), 4.86 (1 H, dd, J 17 and 1 Hz, trans 6-proton), 4.83 (1 H, dd, J 8 and 6.5 Hz, 17- proton), 3.82 (3 H, s, OCH$_3$), 3.81 (1 H, dd, J 11 and 2 Hz, 8-proton), 2.70 (1 H, dt, J 11 and 2 Hz, 14-proton), 2.25–1.40 (6 H, m) 1.37 (3 H, s, 18-CH$_3$), 1.15 (9 H, s, OBu$^t$);

(Found: M+ 510.2467. C$_{30}$H$_{38}$O$_5$S requires M 510.2439).

9α,11α-Epoxy-3-methoxy-8ξ-phenylsulphonyl-8,9-seco-5,6-secoestra-1,3,5(10),6-tetraene-17β-yl acetate (10) and its 9β, 11β-isomer (11).

Dry potassium fluoride (70 mg, 1.2 mmol) was added to a stirred solution of m-chloroperbenzoic acid (191 mg, 1.11 mmol) in dry dichloromethane (25 ml). After stirring at room temperature for 15 min, a solution of the acetoxy-sulphone (9) (173 mg, 0.37 mmol) in dry dichloromethane (2 ml) was added, and the mixture was stirred for a further 24 h at room temperature. The mixture was filtered, and the filtrate was treated with more potassium fluoride (70 mg, 1.2 mmol) for 10 min, with vigorous stirring. After a further filtration, the filtrate was evaporated under reduced pressure to give a mixture of the crude products (10) and (11), (180 mg, quantitative), $\nu_{max}$ 1730 cm$^{-1}$ (CO), δ 7.82–7.12 (7 H, m, aromatic protons), 6.85 (2 H, d, J 8 Hz, 2- and 4-protons), 5.85 (1 H, m, 7-proton), 5.25 (1 H, d, J 10 Hz, cis 6-proton), 4.89 (1 H, d, J 17 Hz, trans 6-proton), 4.91 (1 H, m, 17-proton), 3.78 (3 H, s, OCH$_3$), 3.70 (1 H, m, 8-proton), 3.54 and 3.50 (1 H, 2 s, 9-proton), 2.96 (1 H, m, 11-proton), 2.64 (1 H, d, J 11 Hz, 14-proton), 2.2 (1 H, m), 2.04–1.4 (5 H, m), 1.90 and 1.51 (3 H, 2 s, COCH$_3$), 0.90 and 0.87 (3 H, 2 s, 18—CH$_3$), (Found: M+ 482. C$_{27}$H$_{32}$O$_6$ requires M 482), in the ratio 1:1 according to n.m.r. spectroscopy. The mixture could not be purified by chromatography, since the compounds decomposed on contact with silica and alumina. It was therefore used in the crude state for the next step.

3-Methoxy-9α,11α-epoxy-8ξ-phenylsulphonyl-8,9-seco-5,6-secoestra-1,3,5(10),6-tetraene-17β-yl trimethylacetate (10B), and its 9β,11β-isomer (11B).

Oxidation of the olefin (9B) (850 mg) in the above manner gave a mixture of the epoxides (10B) and (11B) (880 mg, quantitative), in the ratio 2:1, δ 7.81–7.14 (7 H, m, aromatic protons), 6.87 (2 H, d, J 8 Hz, 2- and 4-protons), 5.88 (1 H, two dt, J 17 and 10 Hz, 7-proton), 5.27 (1 H, two dd, J 10 and 1 Hz, cis-6-proton), 4.89 (1 H, dd, J 17 and 1 Hz, trans-6-proton), 4.82 (1 H, m, 17-proton), 3.80 (3 H, s, OCH$_3$), 3.72 (1 H, m, 8-proton), 3.53 (1 H, two d, J 2 Hz, 9-proton), 3.00 (1 H, m), 1.14 and 1.13 (9 H, two s, OBu$^t$), 0.97 and 0.95 (3 H, two s, 18-CH$_3$). When the oxidation was carried out at 0° C. for two days, the epoxides were obtained in the ratio 3.3:1. The crude epoxides were used directly for the next step, because they decomposed on chromatography.

3-Methoxy-9α,11α-epoxy-8ξ-phenylsulphonyl-8,9-seco-5,6-secoestra-1,3,5(10),6-tetraene-17-one (10C) and its 9β,11β-isomer (11C).

Oxidation of the unsaturated keto sulphone (7) (192 mg) in the above manner gave a mixture (203 mg, quantitative) of the epoxides (10C) and (11C), in the ratio 1:1 according to its n.m.r. characteristics, δ 7.84–7.15 (7 H, m, aromatic protons), 6.88 (2 H, d, J 8 Hz, 2- and 4-protons), 5.89 (1 H, two dt, J 17 and 10 Hz, 7-proton), 5.25 (1 H, two dd, J 10 and 1 Hz, cis-6-proton), 4.86 (1 H, two d, J 17 Hz, trans-6-proton), 3.88–3.79 (1 H, m, 8-proton), 3.80 (3 H, s, OCH$_3$), 3.71 and 3.55 (1 H, two d, J 4 Hz, 9-proton), 3.29–3.05 (2 H, m, 11- and 14-protons), 2.51–1.87 (5 H, m), 0.96 and 0.94 (3 H, two s, 18-CH$_3$), (Found: M+ 440.1663. C$_{25}$H$_{28}$O$_5$S requires M 440.1657).

3-Methoxy-9α,11α-epoxy-8ξ-phenylsulphonyl-8,9-seco-5,6-secoestra-1,3,5(10),6-tetraene-17-ethylene ketal (10E), and its 9β,11β-isomer (11E).

Oxidation of the unsaturated keto sulphone acetal (7E) (110 mg) in the above manner gave a mixture (121 mg, quantitative) of the epoxides (10E) and (11E) in the ratio 1:1 according to its n.m.r. characteristics, $\nu_{max}$ 1140 cm$^{-1}$ (SO$_2$), δ 7.83–7.13 (7 H, m, aromatic protons), 6.86 (2 H, d, J 8 Hz, 2- and 4-protons), 5.92 (1 H, m, 7-proton), 5.23 (1 H, d, J 10 Hz, cis-6-proton), 4.85 (1 H, two dd, J 17 Hz, trans-6-proton), 4.02–3.67 (5 H, m, OCH$_2$CH$_2$O and 8-proton), 3.78 (3 H, s, OCH$_3$), 3.56 and 3.53 (1 H, two s, 9-proton), 3.22–2.94 (2 H, m, 11- and 14-proton), 2.42–1.49 (7 H, m), 1.01 and 0.93 (3 H, two s, 18-CH$_3$), (Found: M+ 484.1936. C$_{27}$H$_{32}$O$_6$S requires M 484.1919.)

8ξ-Phenylsulphonyl-9α,11α-epoxy-8,9-seco-5,6-secoestra-1,3,5(10)-tetraaene-17β-yl trimethylacetate (10A) and its 9β,11β-isomer (11A).

A solution of the olefin (9A) (210 mg, 0.42 mmol) and m-chloroperbenzoic acid (79 mg, 0.46 mmol) in dry methylene chloride (2 ml) was stirred at 0° C. for 5 hours. The mixture was diluted with dichloromethane, washed with sodium bicarbonate and water, dried and evaporated to give a residue which was chromatographed on silica. Elution with ether-light petroleum (3:10) gave the epoxides (10A) and (11A) (185 mg, 89%) as an inseparable mixture, $\nu_{max}$ 1720 (C=O) and 1145 cm$^{-1}$ (SO$_2$), δ (250 MHz) 7.84–7.31 (10 H, m, aromatic protons), 5.90 (1 H, two dt, J 17 and 10 Hz, 7-proton), 5.28 (1 H, two dd, J 10 and 1 Hz, cis-6-proton), 4.90 (1 H, two dd, J 17 and 1 Hz, trans 6-proton), 4.89 (1 H, two t, J 7.5 Hz, 17-proton), 3.80 (1 H, two dd, J 10 amd 1.5 Hz, 8-proton), 3.58 (1 H, two d, J 2 Hz, 9-proton), 2.98 (1 H, two dt, J 6 and 2 Hz, 11-proton), 2.69 (1 H, two t, J 10 Hz, 14-proton), 2.35–1.40 (m, aliphatic protons), 1.21 and 1.19 (9 H, two singlets, OBu$^t$), 0.97 and 0.91 (3 H, two singlets, ratio 1.67:1, 18-CH$_3$).

(Found: C, 70.0; H, 7.45; S, 6.5. C$_{29}$H$_{36}$O$_5$S requires C, 70.1, H, 7.3; S, 6.45%.). M+ (ammonia chemical ionization 514. C$_{29}$H$_{36}$O$_5$S.NH$_3$ requires 514.

3-Methoxy-6-Tri-n-butylstannyl-9α,11α-epoxy-17β-acetoxy-8,9-seco-5,6-secoestra-1,3,5(10),7-tetraene (1), and its 9β,11β-isomer (3).

2,2-Azobis-2-methylpropionitrile (50 mg, 0.3 mmol) was added to a boiling solution of tri-n-butyltin hydride (7.4 g, 25 mmol) and the allyl sulphones (10) and (11) (4.9 g, 10 mmol) in dry benzene (60 ml) under argon. After 10 min, the solution was cooled, and the solvent was evaporated under reduced pressure to give a crude mixture of the products (1) and (3) (12 g), together with organotin byproducts and some of the cyclized product (2). The crude mixture was used directly for the next step, because it underwent extensive decomposition on chromatography.

3-Methoxy-6-Tri-n-butylstannyl-9α,11α-epoxy-17β-trimethylacetoxy-8,9-seco-5,6-secoestra-1,3,5(10),7-tetraene (1B), and its 9β,11β-isomer (3B).

Treatment of a mixture of the epoxy sulphones (10B) and (11B) (880 mg) in the above manner gave a crude mixture of the epoxy allyl stannanes (1B) and (3B) (2 g) which was used directly for the next step.

3-Methoxy-11α-hydroxy-5,6-seco-9α-estra-1,3,5(10),6-tetraene 17β-yl acetate (2) and 3-methoxy- 11β-hydroxy-5,6-seco-9β-estra-1,3,5(10),6-tetraene-17β-yl acetate (4).

A solution of the crude allyl stannanes (1) and (3) (12 g) from the previous step was treated with dry zinc bromide (3 g, 13.3 mmol) at −78° C. under argon. After being allowed to warm to room temperature overnight the mixture was treated with dilute hydrochloric acid and extracted with ether. The ethereal extract was washed with dilute hydrochloric acid, then with water, dried, and evaporated, to give a residue which was chromatograpahed on silica (100 g), eluted first with ether-light petroleum (3:7) and then with ether-light petroleum (1:1) to give first, the oily 3-methoxy-11β-hydroxy-5,6-seco-9β-estra-1,3,5(10),6-tetraene-17b-yl acetate (4), (1.0 g, ca. 38% from (9), contaminated by some organotin byproduct), $\nu_{max}$ 3450 (OH) and 1730 cm$^{-1}$ (CO), δ (250 MHz) 7.09 (2 H, d, J 8.5 Hz, 1- and 5-protons), 6.81 (2 H, d, J 8.5 Hz, 2- and 4-protons), 5.05 (2 H, m, vinylic protons), 4.82 (2 H, m, vinylic proton, and 17-proton), 4.24 (1 H, dt, J 4.5 and 2.5 Hz, 11-proton), 3.80 (3 H, s, OCH$_3$), 3.08 (1 H, ddd, J 5, 2, and 1 Hz, 9-proton), 2.80 (1 H, m), 2.10 (3 H, s, COCH$_3$), 2.10–2.00 (3 H, m), 1.71–1.33 (5 H, m), 1.15 (3 H, s, 18-CH$_3$);

(Found: M$^+$ 344.1969. C$_{21}$H$_{28}$O$_4$ requires M 344.1987), and then 3-methoxy-11α-hydroxy-5,6-seco-9α-estra-1,3,5(10),6-tetraene-17b-yl acetate (2) (1.1 g, 63% from (9)) as an oil, $\nu_{max}$ 3450 (OH) and 1730 cm$^{-1}$ (CO), δ 7.09 (2 H, d, J 8 Hz, 1- and 5-protons), 6.85 (2 H, d, J 8 Hz, 2- and 4-protons), 5.31 (1 H, ddd, J 16.5, 10, and 8 Hz, 7-proton), 4.74 (1 H, dd, J 10 and 2 Hz, cis-6-proton), 4.72 (1 H, t, J 8 Hz, 17-proton), 4.67 (1 H, dd, J 16.5 and 2 Hz, trans 6-proton), 3.94 (1 H, ddd, J 11.5, 10, 5, and 2.5 Hz, 11-proton), 3.79 (3 H, s, OCH$_3$), 2.45–2.16 (4 H, m), 2.04 (3 H, s, COCH$_3$), 1.53–1.22 (6 H, m), 1.00 (3 H, s, 18-CH$_3$);

(Found: M$^+$ 344.2000. C$_{21}$H$_{28}$O$_4$ requires M 344.1987).

3-Methoxy-11α-hydroxy-5,6-seco-9α-estra-1,3,5(10),6-tetraene-17β-yl trimethylacetate (2B) and 3-methoxy-11β-hydroxy-5,6-seco-9β-estra-1,3,5(10),6-tetraene-17β-yl trimethylacetate (4B).

Treatment of a mixture (2 g) of the crude allyl stannanes (1B) and (3B) in the above manner gave the hydroxy ester (2B) (413 mg, 96% from (10B)), δ 7.10 (2 H, d, J 8.5 Hz, 1- and 5-protons), 6.85 (2 H, d, J 8.5 Hz, 2- and 4-proton), 5.32 (1 H, ddd, J 16.5, 10, and 8 Hz, 7-proton), 4.75 (1 H, dd, J 10 and 2 Hz, cis-6-proton), 4.69 (1 H, dd, J 9 and 7.5 Hz, 17-proton), 4.68 (1 H, dd, J 16.5 and 2 Hz, trans-6-proton), 3.94 (1 H, m, 11-proton), 3.79 (3 H, s, OCH$_3$), 2.38–2.13 (4 H, m), 1.54–1.23 (4 H, m), 1.20 (9 H, s, OBu$^t$), 1.04 (3 H, s, 18-CH$_3$), (Found: M$^+$ 386.2462. C$_{24}$H$_{34}$O$_4$ requires M 386.2457), and the hydroxy ester (4B) (190 mg, 89% from (11B)), δ 7.09 (2 H, d, J 8.5 Hz, 1- and 5-protons), 6.80 (2 H, d, H 8.5 Hz, 2- and 4-protons), 5.09–5.02 (2 H, vinyl protons), 4.88–4.83 (1 H, m, vinyl proton), 4.76 (1 H, dd, J 8.5 and 7 Hz, 17-proton), 4.24 (1 H, dt, J 4 and 2 Hz, 11-proton), 3.79 (3 H, s, OCH$_3$), 3.08 (1 H, d, J 6 Hz, 9-proton), 2.81 (1 H, m, 8-proton), 2.19–1.90 (4 H, m), 1.70–1.23 (4 H, m), 1.20 (9 H, s, OBu$^t$), 1.15 (3 H, s, 18-CH$_3$).

11α-Hydroxy-5,6-seco-9α-estra-1,3,5(10),6-tetraene-17β-yl trimethylacetate (2A) and 11β-hydroxy-5,6-seco-9β-estra-1,3,5(10),6-tetraene-17β-yl trimethylacetate (4A).

Treatment of a mixture (170 mg, 0.34 mmol, α:β ratio 1.67:1) of the epoxides (10A) and (11A) with tri-n-butyltin hydride in the manner described previously gave a crude mixture of the epoxy allyl stannanes (1A) and (3A), which was allowed to react with zinc bromide in the manner described above. Chromatography of the crude product on silica (5 g) eluted with ether-light petroleum (1:10) gave, first, 11β-hydroxy-5,6-seco-9β-estra-1,3,5(10),6-tetraene-17β-yl trimethylacetate (4A), (45 mg, 37%), m.p. 93°–95° C. (from ether-light petroleum), $\nu_{max}$ 1715 cm$^{-1}$ (C═O), δ (250 MHz) 7.30–7.13 (5 H, m, aromatic protons), 5.06–4.81 (3 H, m, protons at 6 and 7), 4.76 (1 H, dd, J 9 and 7 Hz, 17-proton), 4.30–4.23 (1 H, m, 11-proton), 3.12 (1 H, d, J 6 Hz, 9-proton), 2.90–2.77 (1 H, m, 8-proton), 1.71 (9 H, s, OBu$^t$), 1.22 (3 H, s, 18-CH$_3$), m/z 356 (M$^+$), and then 11α-Hydroxy-5,6-seco-9α-estra-1,3,5(10),6-tetraene-17β-yl trimethylacetate (2A) (83 mg, 61%), m.p. 103°–105° C. (from ether-light petroleum), $\nu_{max}$ 1720 cm$^{-1}$ (C═O), δ 7.34–7.13 (5 H, m, aromatic protons), 5.31 (1 H, ddd, J 17, 10, and 8 Hz, 7-proton), 4.70–4.61 (3 H, m, 6- and 17-protons), 3.98 (1 H, ddd, J 10, 9, and 4.5 Hz, 11-proton), 1.20 (9 H, s, OBu$^t$), 1.02 (3 H, s, 18-CH$_3$), m/z 254 (M-102).

3-Methoxy-11α-hydroxy-5,6-secoestra-1,3,5(10),6-tetraene-17-one (2C).

Treatment of the mixture (1:1 g) of epoxy keto sulphones (10C) and (11C) in sequence with tri-n-butyltin hydride and zinc bromide in the manner described above gave, after chromatography on silica, the hydroxy ketone (2C) (125 mg, 33% over two steps) $\nu_{max}$ 3500 (OH) and 1740 cm$_{-1}$ (C═O), δ 7.10 (2 H, d, J 8.5 Hz, 1- and 5-protons), 6.87 (2 H, d, J 8.5 Hz, 2- and 4-protons), 5.37 (1 H, ddd, J 16.5, 10, and 8.5 Hz, 7-proton), 4.84 (1 H, dd, J 10 and 1.5 Hz, cis-6-proton), 4.76 (1 H, ddd, J 16.5, 1.5, and 0,5 Hz, trans-6-proton), 4.00 (1 H, ddd, J 11.5, 10, and 5 Hz, 11-proton), 3.80 (3 H, s, OCH$_3$), 2.53 (1 H, ddd, J 10, 8.5, and 1 Hz, 8-proton), 2.43 (1 H, dt, J 10 and 8.5 Hz, 9-proton), 2.32–1.34 (7 H, m), 1.79 (1 H, br s, OH), 1.08 (3 H, 3 H, s, 18-CH$_3$), (Found: M$^+$ 300.1733. C$_{19}$H$_{24}$O$_3$ requires 300.1725), together with 3-methoxy-11β-hydroxy-5,6-seco-9β-estra-1,3,5(10),6-tetraene-17-one (4C) (130 mg) contaminated with unidentified organotin compounds.

3-Methoxy-11α-hydroxy-5,6-seco-9α-estra-1,3,5(10),6-tetraene-17-ethylene ketal (2E) and
3-methoxy-11β-hydroxy-5,6-seco-9β-estra-1,3,5(10),6-tetraene-17-ethylene ketal (4E).

Treatment of the mixture (116 mg) of epoxy keto sulphones (10E) and (11E) in sequence with tri-n-butyltin hydride and zinc bromide in the manner described above gave, after chromatography on silica, the 11α-alcohol (2E) (18 mg), (44% over two steps) $\nu_{max}$ 3500 cm$^{-1}$ (OH), δ 7.09 (2 H, d, J 8.5 Hz, 1- and 5-protons), 6.85 (2 H, d, J 8.5 Hz, 2- and 4-protons), 5.32 (1 H, ddd, J 16.5, 10, and 8.5 Hz, 7-proton), 4.73 (1 H, dd, J 10 and 2 Hz, cis-6-proton), 4.66 (1 H, dd, J 17 and 2 Hz, trans-6-proton), 3.99–3.89 (4 H, m, OCH$_2$CH$_2$O), 3.79 (3 H, s, OCH$_3$), 2.30–1.20 (11 H, m), 1.05 (3 H, s, 18-CH$_3$), (Found: M$^+$ 344.1996. C$_{21}$H$_{28}$O$_4$ requires 344.1987). The 11b-alcohol (4E) (14 mg), $\nu_{max}$ 3500 cm$^{-1}$ (OH), δ (250 MHz) 7.05 (2 H, J 8 Hz, 1- and 5-protons), 6.82 (2 H, d, J 8 Hz, 2-and 4-protons), 5.15–4.90 (3 H, m, vinylic protons), 4.24 (1 H, m, 11-proton), 3.96 (4 H, m, OCH$_2$CH$_2$O), 3.79 (3 H, s, OCH$_3$), 3.07 (1 H, dd, J 6 and 2 Hz, 9-proton), 2.76 (1 H, ddd, J 10, 8, and 6 Hz, 8-proton), 2.49–1.92 (5 H, m), 1.85–1.10 (3 H, m), 1.05 (3 H, s, 18-CH$_3$), (Found: M+ 344. $C_{21}H_{28}O_4$ requires M 344), was also obtained, contaminated with minor amounts of an unknown organotin compound.

3-Methoxy-5,6-secoestra-1,3,5(10),6-tetraene-11α,17β-diol (12).

A solution of the hydroxy-acetate (2) (291 mg, 0.85 mmol) in dry ether (2 ml) was added dropwise to a stirred solution of lithium aluminium hydride (32 mg, 0.85 mmol) in dry ether (5 ml) at 0° C. After 1 h the excess lithium aluminium hydride was destroyed by careful addition of wet ether, and then water (dropwise), the ethereal solution was decanted off, dried, and evaporated to give the product (12) (250 mg, 98%), $\nu_{max}$ 3400 cm$^{-1}$ (OH), δ 7.13 (2 H, d, J 8 Hz, 1- and 5-protons), 6.89 (2 H, d, J 8 Hz, 2- and 4-protons), 5.33 (1 H, ddd, J 16.5, 10, and 8 Hz, 7-proton), 4.76 (1 H, dd, J 10 and 2 Hz, cis 6-proton), 4.70 (1 H, dd, J 16.5 and 2 Hz, trans 6-proton), 4.00 (1 H, ddd, H 11, 9.5, and 5 Hz, 11-proton), 3.83 (1 H, t, J 9 Hz, 17-proton), 3.82 (3 H, s, OCH$_3$), 2.40–1.13 (9 H, m), 1.71 (2 H, s, OH), 0.99 (3 H, s, 18-CH$_3$);

(Found: M+ 302. $C_{19}H_{26}O_3$ requires M 302).

3-Methoxy-11α,17β-di(trimethylacetoxy)-5,6-secoestra-1,3,5(10),6-tetraene (13).

Trimethylacetyl chloride (0.34 ml, 2.8 mmol) was added to a stirred suspension of dry silver cyanide (75 mg, 0.56 mmol) in a solution of the diol (12) (84 mg, 0.28 mmole) in dry benzene (5 ml) at room temperature. Stirring was continued overnight, after which the solution was diluted with ether (5 ml), filtered, and the filtrate evpaorated under reduced pressure. Chromatography of the residue on silica (1 g) eluted with ether-light petroleum gave the product (13) (120 mg, 92%), m.p. 114°–5° C. (from ether-light petroleum), $\nu_{max}$ 1730 cm$^{-1}$ (CO), δ (250 MHz) 7.12 (2 H, d, J 8.5 Hz, 1- and 5-protons), 6.77 (2 H, d, J 8.5 Hz, 2- and 4-protons), 5.33 (1 H, ddd, J 16.5, 10, and 8 Hz, 7-proton), 5.24 (1 H, dt, H 11, and 5 Hz, 11-proton) 4.77 (1 H, dd, J 10 and 2 Hz, cis 6-proton), 4.70 (1 H, dd, J 9 and 7.5 Hz, 17-proton), 4.69 (1 H, dd, J 16.5 and 2 Hz, trans 6-proton), 3.75 (3 H, s, OCH$_3$), 2.48 (1 H, t, J 11 Hz, 9-proton), 2.42–2.18 (2 H, m), 2.12 (1 H, dd, J 12 and 5 Hz, 12-proton), 1.67–1.23 (5 H, m), 1.21 (9 H, s, OBu$^t$), 1.09 (1 H, s, 18-CH$_3$), 0.89 (9 H, s, OBu$^t$);

(Found: (ammonia chemical ionization) M+ 488. $C_{29}H_{42}O_5 \cdot NH_4$ requires M 488).

11α,17β-Di(trimethylacetoxy)-5,6-secoestra-1,3,5(10),6-tetraene (13A).

Esterification of the diol (12A) (0.5 g) in the above manner gave the diester (13A) (0.788 g, 97%), m.p. 121°–124° C. (from ether-light petroleum), $\nu_{max}$ 1724 cm$^{-1}$ (CO), δ (250 MHz) 7.27–7.06 (5 H, m, aromatic protons), 5.41–5.22 (2 H, m, 7- and 11-protons), 4.77–4.62 (3 H, m, 6-and 17-proton), 2.52 (1 H, t, J 10.5 Hz, 9-proton), 2.45–2.09 (3 H, m), 1.64–1.24 (5 H, m), 1.20 (9 H, s, OBu$^t$), 1.09 (1 H, s, 18-CH$_3$), 0.86 (9 H, s, OBu$^t$);

(Found: M+ 440.2945. $C_{28}H_{40}O_4$ requires M 440.2924). Esterification of the hydroxy ester (2A) (162 mg) with trimethylacetyl chloride in the above manner also gave the diester (13A) (188 mg, 93%).

3-Methoxy-11α,17β-di(trimethylacetoxy)-5,6-secoestra-1,3,5(10)-triene-6-ol (14).

A solution of monochloroborane-dimethyl sulphide complex (290 mg, 2.6 mmole) and the olefin (13) (120 mg, 0.26 mmole) in dry dichloromethane (5 ml) was kept at 0° C. for 3 h, and then treated with ether (5 ml) and aqueous hydrogen peroxide (30%, 1 ml). After stirring overnight, the mixture was diluted with water, extracted with ether, and the ethereal extract washed with water, dried, and evaporated. Chromatography of the residue on silica (2 g) eluted with ether-light petroleum (2:5) gave the product (14) (104 mg, 84%), $\nu_{max}$ 3500 (OH) and 1720 cm$^{-1}$ (CO), δ (250 MHz) 7.09 (2 H, d, J 8 Hz, 1- and 5-protons), 6.80 (2 H, d, J 8 Hz, 2- and 4-protons), 5.17 (1 H, dt, H 11 and 5 Hz, 11-proton) 4.66 (1 H, dd, J 9 and 7.5 Hz, 17-proton), 3.35 (2 H, m, 6-protons), 3.78 (3 H, s, OCH$_3$), 2.41 (1 H, t, J 11 Hz, 9-proton), 2.32–2.05 (2 H, m), 1.95–1.74 (2 H, m), 1.62–1.23 (7 H, m), 1.20 (9 H, s, OBu$^t$), 1.07 (1 H, s, 18-CH$_3$), 0.89 (9 H, s, OBu$^t$);

(Found: M+ 506 (ammonia chemica ionization). $C_{29}H_{44}O_6 \cdot NH_4$ requires 506).

11α,17β-Di(trimethylacetoxy)-5,6-secoestra-1,3,5(10)-triene-6-ol (14A).

Treatment of the unsaturated diester (13A) (1.241 g) in the above manner gave the hydroxy diester (14A) (1.062 g, 82%), m.p. 128°–131° C. (from ether-light petroleum), $\nu_{max}$ 3600 (OH) and 1720 cm$^{-1}$ (CO), δ (250 MHz) 7.29–7.12 (5 H, m, aromatic protons), 5.20 (1 H, dt, H 11 and 4 Hz, 11-proton) 4.65 (1 H, dd, J 9 and 7 Hz, 17-proton), 3.46–3.23 (2 H, m, 6-protons), 2.30 (1 H, m), 2.10 (1 H, dd, J 11.5 and 4 Hz, 12-proton), 2.00–1.4 (9 H, m), 1.19 (9 H, s, OBu$^t$), 1.07 (1 H, s, 18-CH$_3$), 0.83 (9 H, s, OBu$^t$); M+ (ammonia chemical ionization) 476.

(Found: C, 73.5; H, 9.0. $C_{28}H_{42}O_5$ requires C, 73.3; H, 9.3%)

3-Methoxy-11α,17β-di(trimethylacetoxy)-5,6-secoestra-1,3,5(10)-triene-6-oic acid (15).

Jones reagent (0.2 ml) was added dropwise to a stirred solution of the alcohol (14) (155 mg, 0.3 ml) in dry acetone (3 ml) at 0° C. After 30 min at 0° C., propan-2-ol (2 ml) was added and the solvent removed by evaporation under reduced pressure. The residue was partitioned between ether and dilute hydrochloric acid, and the ether extract was washed with water, dried, and evaporated. Chromatography of the residue on silica (2 g) eluted with ether-light petroleum (4:1) gave the product (15) (131 mg, 82%), m.p. 167°–9° C. (from light petroleum), $\nu_{max}$ 1720 cm$^{-1}$ (CO), δ (250 MHz) 7.10 (2 H, d, J 8 Hz, 1- and 5-protons), 6.79 (2 H, d, J 8 Hz, 2- and 4-protons), 5.23 (1 H, dt, H 11 and 4.5 Hz, 11-proton), 4.67 (1 H, dd, J 9 and 6.5 Hz, 17-proton), 3.73 (3 H, s, OCH$_3$), 2.48 (1 H, t, J 11 Hz, 9-proton), 2.32–2.06 (6 H, m), 1.75–1.45 (4 H, m), 1.20 (9 H, s, OBu$^t$), 1.09 (1 H, s, 18-CH$_3$), 0.86 (9 H, s, OBu$^t$);

(Found: C, 69.6; H, 8.2; M+ 520 (ammonia chemical ionization). $C_{29}H_{42}O_7$ requires C, 69.3; H, 8.4%; $C_{29}H_{42}O_7 \cdot NH_4$ requires M 520).

11α,17β-di(trimethylacetoxy)-5,6-secoestra-1,3,5(10)-triene-6-oic acid (15A).

Oxidation of the hydroxy diester (14A) (105 mg) in the above manner gave the acid (15A) (87 mg, 81%), m.p. 230°–231° C. (from ether-light petroleum), $\nu_{max}$ 1720 cm$^{-1}$ (CO), δ 7.32–7.13 (5 H, m, aromatic protons), 5.26 (1 H, dt, J 10.5 and 4.5 Hz, 11-proton), 4.69 (1 H, dd, J 9 and 7 Hz, 17-proton), 2.69 (2 H, ABX system, J 17, 6.5, and 3.5 Hz, 7-protons), 2.53 (1 H, t, J 10.5 Hz, 11-proton), 2.4–1.2 (9 H, m), 1.20 (9 H, s, OBu$^t$), 1.09 (3 H, s, 18-CH$_3$), 0.82 (9 H, s, OBu$^t$), M+ (ammonnia chemical ionization) 490 (M+NH$_3$), (Found: C, 71.2; H, 8.3. $C_{28}H_{40}O_6$ requires C, 71.2; H, 8.5%).

3-Methoxy-11α,17β-di(trimethylacetoxy)-estra-1,3,5(10)-triene-6-one (16).

A stirred solution of the acid (15) (151 mg, 0.3 mmole) in dry benzene (3 ml) at room temperature under argon was treated with sodium hydride (8 mg, 0.33 mmol, free of mineral oil). After 15 min, oxalyl chloride (0.26 ml, 3 mmol) was added, the solution kept at 40° C. for 1 h, and the solvent evaporated under reduced pressure. The residue was dissolved in dry dichloromethane (5 ml) and treated with freshly ground aluminium chloride (402 mg, 3 mmol). After 30 min at room temperature water (5 ml) was added, and the mixture was extracted with ether (3×15 ml). The ethereal extract was washed in succession with dilute hydrochloric acid, sodium hydroxide, and water, dried, and evaporated to give a residue which was chromatographed on silica (2 g). Elution with ether-light petroleum (1:5) gave the product (16) (140 mg, 96%), m.p. 183°-4° C. (from light petroleum), $\nu_{max}$ 1720 and 1680 cm$^{-1}$ (CO), δ (250 MHz) 7.54 (1 H, t, J 1.5 Hz, 4-proton), 7.02 (2 H, d, J 1.5 Hz, 1- and 2-protons), 5.42 (1 H, dt, H 10 and 5.5 Hz, 11-proton), 4.67 (1 H, dd, J 8.5 and 7 Hz, 17-proton), 3.84 (3 H, s, OCH$_3$), 2.82 (1 H, t, J 11 Hz, 9-proton), 2.82 (1 H, dd, J 17 and 3.5 Hz, 12-proton), 2.33 (2 H, AB part of ABX system, J 12 and 5.5 Hz, 7-protons), 2.28 (1 H, m), 2.06 (1 H, qt, J 12, 11, 5.5, and 3.5 Hz, 8-proton), 1.80–1.40 (5 H, m), 1.22 (9 H, s, OBu$^t$), 1.21 (9 H, s, OBu$^t$), 0.91 (1 H, s, 18-CH$_3$);

(Found: C, 71.8; H, 8.2; M$^+$ 485 C$_{29}$H$_{40}$O$_6$ requires C, 71.9; H, 8.3%; (M+1) 485).

11α,17β-Di(trimethylacetoxy)-estra-1,3,5(10)-triene-6-one (16A).

Treatment of the acid (15A) (172 mg) in sequence with oxalyl chloride and aluminium chloride in the above manner gave the keto diester (16A) (158 mg, 95%), m.p. 186°-187° C. (from ether-light petroleum), $\nu_{max}$ 1720 (C=O) and 1680 cm$^{-1}$ (C=O), δ (250 MHz) 8.05 (1 H, dd, J 7.5 and 2 Hz, aromatic proton), 7.48 (1 H, dt, J 7.5 and 2 Hz, aromatic proton), 7.36 (1 H, dt, J 7.5 and 1 Hz, aromatic proton), 7.11 (1 H, dt, J 7.5 and 1 Hz, aromatic proton), 5.47 (1 H, dt, H 10.5 and 5.5 Hz, 11-proton), 4.68 (1 H, dd, H 9 and 7 Hz, 17-proton), 2.93–2.80 (2 H, m), 2.43–1.25 (9 H, m), 1.22 (9 H, s, OBu$^t$), 1.21 (9 H, s, OBu$^t$), 0.92 (3 H, s, 18-CH$_3$), M+ (ammonia chemical ionization) 472 (M+NH$_3$), (Found: C, 74.2; H, 8.45. C$_{28}$H$_{38}$O$_5$ requires c, 74.0; H, 8.4%).

3-Methoxy-11α,17β-dihydroxy-estra-1,3,5(10)-triene-6-one (5).

The keto-diester (16) (30 mg, 0.06 mmole) was added to a degassed 10% solution of potassium hydroxide in methanol-water (19:1) (4 ml), and the solution was boiled for 3.5 h under nitrogen. The solvent was removed by evaporation under reduced pressure, and the residue was dissolved in ether. The residue was washed in succession with dilute hydrochloric acid and water, dried, and evaporated to give a residue which was chromatographed on silica (1 g) eluted with ether to give the product (5) (16 mg, 82%), m.p. 113°-4° C. (from ether-light petroleum), $\nu_{max}$ 3400 (OH) and 1675 cm$^{-1}$ (CO), δ (400 MHz) 8.08 (1 H, dd, J 8.5 and 1 Hz, 1-proton), 7.54 (1 H, d, J 3 Hz, 4-proton), 7.12 (1 H, dd, H 8.5 and 3 Hz, 2-proton), 4.27 (1 H, dt, H 10 and 5 Hz, 11-proton), 3.85 (3 H, s, OCH$_3$), 3.79 (1 H, t, J 8 Hz, 17-proton), 2.78 (1 H, dd, J 17 and 2,5 Hz, 12-proton), 2.45 (1 H, t, J 10 Hz, 9-proton), 2.35 (1 H, A portion of ABX system, J 12 and 5 Hz, 7-proton), 2.35 (1 H, B portion of ABX system, J 12 and 5 Hz, 7-proton), 2.18 (2 H, m), 1.96 (1 H, qt, J 14, 10, 5, and 3.5 Hz, 8-proton), 1.86 (2 H, br s, OH), 1.56–1.27 (5 H, m), 0.8 (3 H, s, 18-CH$_3$);

(Found: M$^+$ 316. C$_{19}$H$_{24}$O$_4$ requires M 316).

11α,17β-Dihydroxy-estra-1,3,5(10)-triene-6-one (5A).

Hydrolysis of the keto diester (16A) (158 mg) in the above manner gave the keto diol (5A) (74 mg, 74%), m.p. 205°-208° C. (from methanol, $\nu_{max}$ 3600 (OH) and 1680 cm$^{-1}$ (C=O), δ (250 MHz) 8.13 (1 H, dd, J 8 and 0.5 Hz, aromatic proton), 8.04 (1 H, dd, J 7 and 1,5 Hz, aromatic proton), 7.56 (1 H, dt, J 8 and 1.5 Hz, aromatic proton), 7.36 (1 H, dt, J 7 and 0.5 Hz, aromatic proton), 4.32 (1 H, ddd, J 10.5, 9.5, and 5 Hz, 11-proton), 3.79 (1 H, t, J 8 Hz, 17-proton), 2.77 (1 H, dd, J 17 and 3.5 Hz, 7-proton), 2.5 (1 H, t, J 10.5 Hz, 9-proton), 2.41–1.22 (11 H, m), 0.79 (3 H, s, 18-CH$_3$), (Found: M 286.1572. C$_{18}$H$_{22}$O$_3$ requires M 286.1567).

3-Methoxy-17β-acetoxy-5,6-seco-9β-estra-1,3,5(10),6-tetraene-11-one (17).

Jones reagent (2 ml) was added dropwise to a stirred solution of the crude 11β-alcohol (4) (2 g) in dry acetone (30 ml) at 0° C. After 30 min propan-2-ol (10 ml) was added, and the solvent was evaporated under reduced pressure. The residue was treated with dilute hydrochloric acid (20 ml) and extracted with ether (3×30 ml). The combined ethereal extracts were washed with water, dried, and evaporated to give a residue which was chromatographed on silica (25 g). Elution with ethyl acetate-light petroleum (3:10) gave the product (17) (811 mg) as an oil, $\nu_{max}$ 1730 and 1710 cm$^{-1}$ (CO), δ (400 MHz) 7.18 (2 H, d, J 8 Hz, 1- and 5-protons), 6.83 (2 H, d, J 8 Hz, 2- and 4-protons), 5.26 (1 H, ddd, J 16.5, 10, and 9 Hz, 7-proton), 5.03 (1 H, dd, J 16.5 and 2 Hz, trans 6-proton), 4.90 (1 H, t, J 9 Hz, 17-proton), 4.89 (1 H, dd, J 10 and 2 Hz, cis 6-proton), 3.79 (3 H, s, OCH$_3$), 3.64 (1 H, d, J 6.5 Hz, 9-proton), 2.75–2.67 (1 H, m, 8-proton), 2.60 (2 H, AB system, J 14 Hz, 12-protons), 2.38–2.25 (1 H, m, 14-proton), 2.08 (3 H, s, COCH$_3$), 1.74–1.25 (4 H, m), 0.92 (3 H, s, 18-CH$_3$);

(Found: M$^+$ 342. C$_{21}$H$_{26}$O$_4$ requires M 342).

3-Methoxy-17β-acetoxy-5,6-secoestra-1,3,5(10),6-tetraene-11-one (18).

(a) A solution of the ketone (17) (800 mg, 2.3 mmol) and 1,8-diazabicyclo[5.4.0]undec-7-ene (355 mg, 2.3 mmol) in dry dichloromethane (40 ml) was boiled for 3 h, cooled, washed with dilute hydrochloric acid and water, dried, and evaporated to give the product (18) (791 mg, 99%), m.p. 92 °-93° C., $\nu_{max}$ 1740 and 1705 cm$^{-1}$, δ (400 MHz) 6.93 (2 H, d, J 8 Hz, 1- and 5-protons), 6.86 (2 H, d, J 8 Hz, 2- and 4-protons), 5.45 (1 H, ddd, J 16, 10, and 8 Hz, 7-proton), 4.92 (1 H, t, J 8 Hz, 17α-proton), 4.84 (1 H, dd, J 10 and 1 Hz, cis 6-proton), 4.74 (1 H, dd, J 16 and 1 Hz, trans 6-proton), 3.70 (3 H, s, OCH$_3$), 3.21 (1 H, d, J 11 Hz, 9-proton), 2.53 (2 H, AB system, J 13 Hz, 12-protons), 2.56 (1 H, ddd, J 11, 8, and 8 Hz, 8-proton), 2.35–2.25 (1 H, m, 16-proton), 2.07 (3 H, s, COCH$_3$), 2.05–1.97 (1 H, m, 14-proton), 1.81–1.40 (3 H, m,), 0.94 (3 H, s, 19-CH$_3$);

(Found: C, 73.4; H, 7.4; M$^+$ 342. C$_{21}$H$_{26}$O$_4$ requires C, 73.7; H, 7.6%; M 342).

(b) Jones reagent (0.2 ml) was added dropwise to a stirred solution of the 11α-alcohol (2) (70 mg) in dry acetone (2 ml) at 0° C. After 30 min propan-2-ol (1 ml) was added, and the solvent was evaporated under reduced pressure. The residue was treated with dilute hydrochloric acid (2 ml) and extracted with ether (3×10 ml). The combined ethereal extracts were washed with water, dried, and evaporated to give a residue which was chromatographed on silica (1 g). Elution with ether-light petroleum (1:1) gave the product (18) (58 mg, 83%), identical to the sample prepared above.

3-Methoxy-17β-acetoxy-5,6-secoestra-1,3,5(10),6-tetraene-11β-ol (19).

Sodium borohydride (70 mg, 1.85 mmol) was added to a solution of the keto-ester (18) (126 mg, 0.37 mmol) in dry ethanol (5 ml) at 20° C. After 60 min dilute hydrochloric acid was added, the solvent was evaporated under reduced pressure, and the residue was partitioned between ether and water. The ethereal extract was washed with dilute hydrochloric acid and water, dried and evaporated to give a residue which was chromatographed on silica (2 g). Elution with ethyl acetate-light petroleum (3:10) gave the product (19) (104 mg, 82%) as an oil, $\nu_{max}$ 3420 (OH) and 1730 cm$^{-1}$ (CO), δ (250 MHz) 7.12 (2 H, d, J 8.5 Hz, 1- and 5-protons), 6.86 (2 H, d, J 8.5 Hz, 2- and 4-protons), 5.32 (1 H, ddd, J 17, 10, and 8.5 Hz, 7-proton), 4.92 (1 H, ddd, J 17, 2, and 0.5 Hz, trans 6-proton), 4.85 (1 H, dd, J 10 and 2 Hz, cis-6-proton), 4.68 (1 H, dd, J 9 and 7 Hz, 17-proton), 3.96 (1 H, dt, J 3.5 and 2 Hz, 11-proton), 3.28 (3 H, s, OCH$_3$), 2.75 (1 H, ddd, J 11 and 8.5 Hz, 8-proton), 2.59 (1 H, dd, J 11 and 3 Hz, 9-proton), 2.19–2.12 (2 H, m, 12-protons), 2.06 (3 H, s, COCH$_3$), 1.63–1.31 (5 H, m), 1.15 (3 H, s, 18-CH$_3$);

(Found: M$^+$ 344. C$_{21}$H$_{28}$O$_4$ requires M 344), and its isomer (2) (18 mg, 12%), identical with an authentic sample.

3-Methoxy-11β,17β-diacetoxy-5,6-secoestra-1,3,5(10),6-tetraene (20).

A solution of the hydroxy-ester (19) (50 mg, 0.15 mmol) in dry benzene (2 ml) was treated with dry silver cyanide (39 mg, 0.3 mmol) and acetyl chloride (118 mg, 1.5 mmol) at room temperature. After 16 h ether (2 ml) was added, the solution was filtered through Hyflosupercel, and the filtrate evaporated under reduced pressure. Chromatography of the residue on silica (1 g) eluted with ethyl acetate-light petroleum (3:10) gave the product (20) (53 mg, 94%), $\nu_{max}$ 1740 cm$^{-1}$ (CO), δ (250 MHz) 7.07 (2 H, d, J 8 Hz, 1- and 5-protons), 6.77 (2 H, d, J 8 Hz, 2-and 4-protons), 5.30 (1 H, ddd, J 17, 10, and 8 Hz, 7-proton), 5.12 (1 H, dt, J 3.5 and 2 Hz, 11-proton), 4.90 (1 H, dd, J 17 and 2 Hz, trans 6-proton), 4.85 (1 H, dd, J 10 and 2 Hz, cis-6-proton), 4.67 (1 H, dd, J 9 and 6.5 Hz, 17-proton), 3.76 (3 H, s, OCH$_3$), 2.74 (1 H, m), 2.60 (1 H, dd, J 11 and 3.5 Hz, 9-proton), 2.18–2.06 (2 H, m) 2.04 (3 H, s, COCH$_3$), 1.86 (3 H, s, COCH$_3$), 1.71–1.34 (5 H, m), 1.07 (3 H, s, 18-CH$_3$);

(Found: M$^+$ 386. C$_{23}$H$_{30}$O$_5$ requires M 386).

3-Methoxy-11β,17β-diacetoxy-5,6-secoestra-1,3,5(10)-triene-6-ol (21).

A solution of monochloroborane-dimethyl sulphide complex (781 mg, 7 mmole) and the olefin (20) (272 mg, 0.7 mmole) in dry dichloromethane (8 ml) was kept at 0° C. for 2.5 h, and then treated with ether (8 ml), water (10 ml) and aqueous hydrogen peroxide (30%, 3 ml). After stirring for 2 h at 20° C., the mixture was extracted with ether, and the extract was washed with water, dried, and evaporated. Chromatography of the residue on silica (4 g) eluted with ethyl acetate-light petroleum (2:5) gave the product (21) (242 mg, 85%), $\nu_{max}$ 3420 (OH) and 1730 cm$^{-1}$ (CO), δ (250 MHz) 7.12 (2 H, d, J 8 Hz, 1- and 5-protons), 6.80 (2 H, d, J 8 Hz, 2- and 4-protons), 5.05 (1 H, dt, J 3 and 2.5 Hz, 11-proton), 4.63 (1 H, dd, J 9 and 6.5 Hz, 17-proton), 3.78 (3 H, s, OCH$_3$), 3.47 (2 H, ddt, J 15, 13, 10, and 6 Hz, 6-protons), 2.53 (1 H, dd, J 12 and 3 Hz, 9-proton), 2.32–2.15 (2 H, m), 2.11 (1 H, dd, J 14.5 and 2.5 Hz, 12-proton), 2.04 (3 H, s, COCH$_3$), 1.88 (3 H, s, COCH$_3$), 1.83–1.37 (7 H, m), 1.04 (3 H, s, 18-CH$_3$); (Found: M$^+$ 404. C$_{23}$H$_{32}$O$_6$ requires M 404), and its 7-hydroxy regioisomer 6%).

3-Methoxy-11β,17β-diacetoxy-5,6-secoestra-1,3,5(10)-triene-6-oic acid (22).

Jones reagent (1 ml) was added dropwise to a stirred solution of the alcohol (21) (120 mg, 0.3 mmole) in dry acetone (5 ml) at 0° C. After 30 min at 0° C., propan-2-ol (2 ml) was added and the solvent removed by evaporation under reduced pressure. The residue was partitioned between ether and dilute hydrochloric acid, and the ether extract was washed with water, dried, and evaporated. Chromatography of the residue on silica (2 g) eluted with ether-light petroleum (1:1) gave the product (22) (101 mg, 81%), $\nu_{max}$ 1730 and 1710 cm$^{-1}$ (CO), δ (250 MHz) 7.13 (2 H, d, J 8.5 Hz, 1- and 5-protons), 6.80 (2 H, d, J 8.5 Hz, 2- and 4-protons), 5.10 (1 H, dt, J 3 and 2.5 Hz, 11-proton), 4.65 (1 H, dd, J 9 and 6.5 Hz, 17-proton), 3.77 (3 H, s, OCH$_3$), 2.70–2.60 (1 H, m), 2.59 (1 H, dd, J 11 and 3 Hz, 9-proton), 2.32–2.09 (3 H, m), 2.04 (3 H, s, COCH$_3$), 1.90 (3 H, s, COCH$_3$), 1.80–1.50 (6 H, m), 1.08 (3 H, s, 18-CH$_3$); (Found: M$^+$ 418. C$_{23}$H$_{30}$O$_7$ requires M 418).

3-Methoxy-11β,17β-diacetoxy-estra-1,3,5(10)-triene-6-one (23).

A stirred solution of the acid (22) (44 mg, 0.105 mmole) in dry benzene (5 ml) at room temperature under argon was treated with sodium hydride (2.5 mg, 0.105 mmol, free of mineral oil). After 10 min, oxalyl chloride (0.1 ml, 1.15 mmole) was added, the solution kept at 40° C. for 1 h, and the solvent evaporated under reduced pressure. The residue was dissolved in dry dichloromethane (5 ml) and treated with freshly ground aluminium chloride (141 mg, 1.05 mmole). After 30 min at room temperature water (5 ml) was added, and the mixture was extracted with ether (3×10 ml). The ethereal extract was washed in succession with dilute hydrochloric acid and water, dried, and evaporated to give a residue which was chromatographed on silica (1 g). Elution with ether-light petroleum (3:10) gave the product (23) (42 mg, 99%), m.p. 199°–200° C. (from ether-light petroleum), $\nu_{max}$ 1720 and 1675 cm$^{-1}$ (CO), δ (250 MHz) 7.57 (1 H, t, J 2 Hz, 4-proton), 7.07 (2 H, d, 1- and 2-protons), 5.84 (1 H, dt, J 3 and 2 Hz, 11-proton), 4.69 (1 H, dd, J 9 and 7 Hz, 17-proton), 3.83 (3 H, s, OCH$_3$), 2.81 (1 H, dd, J 14.5 and 3 Hz, 12-proton), 2.80 (1 H, dd, J 11 and 3 Hz, 9-proton), 2.23 (2 H, m), 2.22 (2 H, AB part of ABX system, J 11.5 and 2.5 Hz, 7-protons), 2.04 (3 H, s, COCH$_3$), 1.88 (3 H, s, COCH$_3$), 1.82–1.42 (5 H, m), 0.96 (3 H, s, 18-CH$_3$);

(Found: M$^+$ 400. C$_{23}$H$_{28}$O$_6$ requires M 400).

3-Methoxy-11β,17β-dihydroxy-estra-1,3,5(10)-triene-6-one (6A).

The keto-diester (23) (21 mg, 0.05 mmole) was added to a degassed 10% solution of potassium hydroxide in methanol-water (19:1) (4 ml), and the solution was boiled for 15 min under nitrogen. The solvent was removed by evaporation under reduced pressure, and the residue was dissolved in ether. The extract was washed in succession with dilute hydrochloric acid and water, dried, and evaporated to give a residue which was chromatographed on silica (1 g) eluted with ether to give the product (6A) (15 mg, 90%), m.p. 225°–6° C. (from ether-light petroleum), $\nu_{max}$ 3460 (OH) and 1655 cm$^{-1}$ (CO), δ (250 MHz) 7.61 (1 H, d, J 2.5 Hz, 4-proton), 7.37 (1 H, d, J 8 Hz, 1-proton), 7.17 (1 H, dd, J 8 and 2.5 Hz, 2-proton), 4.84 (1 H, dt, H 3 and 2.5 Hz, 11-proton), 3.85

(3 H, s, OCH$_3$), 3.74 (1 H, dd, J 9 and 7 Hz, 17-proton) 2.78 (1 H, dd, J 15 and 2.5 Hz, 12-proton), 2.71 (1 H, dd, J 10.5 and 2.5 Hz, 9-proton), 2.44 (10 H, m), 1.04 (3 H, s, 18-CH$_3$);

(Found: M$^+$ 316. C$_{19}$H$_{24}$O$_4$ requires M 316).

6-Chloro-3-methoxy-11$\beta$,17$\beta$-dihydroxy-estra-1,3,5(10)-triene (24).

A solution of triphenyl phosphine (107 mg, 0.41 mmol) and the alcohol (21) (110 mg, 0.27 mmol) in dry carbon tetrachloride (5 ml) was refluxed for 16 h under nitrogen, then cooled, and the solvent evaporated under reduced pressure. The residue was chromatographed on silica (2 g) eluted with ether-light petroleum (3:10) to give the product (24) (72 mg, 62%), m.p. 150°-1° C., $\nu_{max}$ 1730 cm$^{-1}$ (CO), δ (250 MHz) 7.11 (2 H, d, J 8.5 Hz, 1- and 5-protons), 6.81 (2 H, d, J 8.5 Hz, 2- and 4-protons), 5.05 (1 H, dt, J 3.5 and 2 Hz, 11-proton), 4.64 (1 H, dd, J 9 and 6.5 Hz, 17-proton), 3.79 (3 H, s, OCH$_3$), 3.30 (2 H, dt, J 8 and 2.5 Hz, 6-protons), 2.48 (1 H, dd, J 11.5 and 3.5 Hz, 9-proton), 2.36–2.16 (2 H, m), 2.11 (1 H, dd, J 14.5 and 2.5 Hz, 12-proton), 2.05 (3 H, s, COCH$_3$), 1.90 (3 H, s, COCH$_3$), 1.85–1.30 (7 H, m), 1.05 (3 H, s, 18-CH$_3$).

11$\beta$,17$\beta$-Diacetoxy-3-methoxy-estra-1,3,5(10)-triene (25).

Freshly ground aluminium chloride (171 mg, 1.3 mmol) was added to a stirred solution of the chloride (24) (54 mg, 0.13 mmol) in dry dichloromethane (5 ml). After 30 min water (5 ml) was added, and the mixture was extracted with ether (3×15 ml). The extract was washed in succession with dilute hydrochloric acid and water, dried, and evaporated. The residue was chromatographed on silica (1.5 g) eluted with ether-light petroleum (3:10) to give the product (25) (50 mg, 99%), m.p. 214°-215° C., $\nu_{max}$ 1730 cm$^{-1}$ (CO), δ (400 MHz) 6.96 (1 H, d, J 8 Hz, 1-proton), 6.66 (1 H, dd, J 8 and 2.5 Hz, 2-proton), 6.63 (1 H, d, J 2.5 Hz, 4-proton), 5.78 (1 H, dt, J 3 and 2.5 Hz, 11-proton), 4.66 (1 H, dd, J 8.5 and 6.5 Hz, 17-proton), 3.78 (3 H, s, OCH$_3$), 2.95–2.79 (2 H, m), 2.50 (1 H, dd, J 10 and 3 Hz, 9-proton), 2.31–2.14 (1 H, m), 2.21 (1 H, dd, J 14.5 and 2.5 Hz, 12-proton), 2.04 (3 H, s, COCH$_3$), 2.00–1.8 (2 H, m), 1.87 (3 H, s, COCH$_3$), 1.78 (1 H, m), 1.63–1.29 (5 H, m), 0.95 (3 H, s, 18-CH$_3$);

(Found: M$^+$ 336. C$_{23}$H$_{30}$O$_5$ requires M 336).

11$\beta$,17$\beta$-Dihydroxy-3-methoxy-estra-1,3,5(10)-triene (6).

A solution of the diacetate (25) (25 mg, 0.065 mmol) in dry ether (1 ml) was added to a stirred solution of lithium aluminium hydride (5 mg, 0.13 mmol) in dry ether (2 ml) at 0° C. under argon. After 15 min, excess lithium aluminium hydride was destroyed by addition of wet ether and then dropwise addition of water. The ethereal layer was separated, dried, and evaporated, and the residue was chromatographed on silica (1 g) to give the product (6) (18 mg, 91%), m.p. 161°-2° C. (from ether-light petroleum), $\nu_{max}$ 3420 cm$^{-1}$ (OH), δ (250 MHz), 7.21 (1 H, d, J 8 Hz, 1-proton), 6.76 (1 H, dd, J 8 and 2.5 Hz, 2-proton), 6.67 (1 H, d, J 2.5 Hz, 4-proton), 4.74 (1 H, m, 11-proton), 3.78 (3 H, s, OCH$_3$), 3.71 (1 H, m, 17-proton), 2.86 (2 H, m, 7-protons), 2.44 (1 H, dd, J 11 and 2 Hz, 9-proton), 2.28 (1 H, dd, J 14 and 2.5 Hz, 12-proton), 2.11 (1 H, qt, J 11, 9, 2.5, and 2 Hz, 8-proton), 1.98–1.31 (7 H, m), 1.61 (2 H, br s OH), 1.03 (3 H, s, 18-CH$_3$);

(Found: M$^+$ 302. C$_{19}$H$_{26}$O$_3$ requires M 302).

3-Methoxy-11$\alpha$,17$\beta$-di(trimethylacetoxy)-estra-1,3,5(10)-triene (26).

Methanesulphonyl chloride (5.4 mg, 0.047 mmol) was added to a stirred solution of the hydroxy diester (14) (21 mg, 0.043 mmol) and triethylamine (7 mg) in dichloromethane (1 ml) at 0° C. After 10 min the solvent was removed by evaporation under reduced pressure to give the crude methanesulphonate, which was dissolved in dry dichloromethane (2 ml) and treated with aluminium trichloride (54 mg, 0.43 mmol). After 30 min at room temperature, water (2 ml) was added, and the mixture was extracted with ether (3×10 ml). The extract was washed with dilute hydrochloric acid and water, dried, evaporated to give a residue which was chromatographed on silica (1 g) eluted with ether-light petroleum (1:9) to give the product (26) (18 mg, 89%), $\nu_{max}$ 1730 cm$^{-1}$ (C=O), δ (250 MHz) 6.92 (1 H, d, J 8 Hz, 1-proton), 6.64 (2 H, m, aromatic protons), 5.38 (1 H, dt, J 10 and 5 Hz, 11-proton), 4.65 (1 H, dd, J 8.5 and 7 Hz, 17-proton), 3.76 (3 H, s, OCH$_3$), 2.83 (2 H, m, 6-protons), 2.49 (1 H, t, J 10 Hz, 9-proton), 2.28 (1 H, A part of ABX system, J 12 and 5 Hz, 12-proton), 1.97–1.31 (8 H, m), 1.20 (18 H, s, two OBu$^t$), 0.89 (3 H, s, 18-CH$_3$), (Found: (ammonia chemical ionization) M$^+$ 488. C$_{29}$H$_{42}$O$_5$.NH$_4$ requires M 488).

11$\alpha$,17$\beta$-Di(trimethylacetoxy)-estra-1,3,5(10)-triene (26A).

Treatment of the hydroxy diester (14A) (343 mg) in sequence with methanesulphonyl chloride and aluminium chloride in the above manner gave the diester (26A) (301 mg, 91%), m.p. 121°-123° C. (from ether-light petroleum), $\nu_{max}$ 1725 cm$^{-1}$ (C=O), δ 7.14–7.07 (3 H, m, aromatic protons), 7.03–6.96 (1 H, m, 1-proton), 5.44 (1 H, dt, J 10.5 and 5 Hz, 11-proton), 4.65 (1 H, dd, J 8.5 and 7 Hz, 17-proton), 2.84 (2 H, dd, J 8 and 7 Hz, 6-protons), 2.54 (1 H, t, J 10.5 Hz, 9-proton), 1.21 (9 H, s, OBu$^t$), 1.19 (9 H, s, OBu$^t$), 0.89 (3 H, s, 18-CH$_3$), M$^+$ (ammonia chemical ionization) 458 (M+NH).

3-Methoxy-estra-1,3,5(10)-11$\alpha$,17$\beta$-diol (6B).

A solution of the methoxy diester (26) (18 mg, 0.04 mmol) in dry ether (0.5 ml) was added to a solution of lithium aluminium hydride (1.56 mg, 0.04 mmol) in ether (1 ml) at 0° C. After 30 min wet ether was added carefully, followed by water dropwise. The ether solution was decanted off, dried, and evaporated to give the product (6B) (11 mg, 91%), m.p. 156°-7° C. (from ether-light petroleum), $\nu_{max}$ 3500 cm$^{-1}$ (OH), δ (250 MHz) 7.86 (1 H, dd, J 8 and 1 Hz, 1-proton), 6.73 (1 H, dd, J 8 and 3 Hz, 2-proton), 6.65 (1 H, d, J 3 Hz, 4-proton), 4.21 (1 H, ddd, J 10.5, 9, and 5 Hz, 11-proton), 3.78 (3 H, s, OCH$_3$), 3.76 (1 H, dd, J 9 and 8 Hz, 17-proton), 2.82 (2 H, t, J 6.5 Hz, 6-proton), 2.29 (1 H, dd, J 12 and 5 Hz, 12-proton), 2.21–1.20 (10 H, m), 1.66 (2 H, br s, OH), 0.81 (3 H, s, 18-CH$_3$), (Found: M$^+$ 302.1877. C$_{19}$H$_{26}$O$_3$ requires M 302.1882).

1,3,5(10)-Estratriene-11$\alpha$,17$\beta$-diol (6C).

Reduction of the diester (26A) with lithium aluminium hydride in the above manner gave the diol (6C) (90%), m.p. 222°-223° C. (from methanol, $\nu_{max}$ 3550 cm$^{-1}$ (OH), δ (MeOH) 7.88–7.82 (1 H, m, 1-proton), 7.12–6.99 (3 H, m, aromatic protons), 4.17 (1 H, ddd, J 10.5, 9.5, and 5 Hz, 11-proton), 3.68 (1 H, dd, J 8.5 and 8 Hz, 17-proton), 2.80 (2 H, t, J 7 Hz, 6-proton), 2.26 (1 H, dd, J 12 and 5 Hz, 12-proton), 2.16 (1 H, t, J 9.5 Hz, 9-proton), 2.10–1.98 (2 H, m, 16-protons), 1.9–0.8 (9 H, m), 0.74 (3 H, s, 18-CH$_3$)

(Found: C, 79.1; H, 8.6; M$^+$ 272.1780. C$_{18}$H$_{24}$O$_2$ requires C 79.4; H, 8.9%; M 272.1776).

2-Acetyl-11α, 17β-di(trimethylacetoxy)-estra-1,3,5(10)-triene (27).

A solution of the diester (26A) (42 mg, 0.095 mmol) and acetyl chloride (0.1 ml, 0.11 g, 1.41 mmol) in dry dichloromethane (1 ml) was treated with anhydrous aluminium chloride (63 mg, 0.47 mmol) at room temperature. After being stirred to 30 min, a saturated aqueous solution of sodium bicarbonate was added, and the mixture was extracted with dichloromethane and worked up in the usual manner to give an oil which was chromatographed on silica (2 g). Elution with ether-light petroleum (1:5) gave the product (27) (43 mg, 93%), as an oil, $\nu_{max}$ 1730 and 1685 cm$^{-1}$ (C=O), δ (250 MHz) 7.75 (1 H, dd, J 8 and 1.5 Hz, 3-proton), 7.64 (1 H, d, J 1.5 Hz, 1-proton), 7.20 (1 H, d, J 8 Hz, 4-proton), 5.52 (1 H, dt, J 10.5 and 5.5 Hz, 11-proton), 4.66 (1 H, dd, J 9 and 7 Hz, 17-proton), 2.89 (2 H, t, J 7 Hz, 6-protons), 2.53 (3 H, s, CH$_3$CO), 2.37–1.25 (11 H, m), 1.23 (18 H, two s, OBu$^t$), 0.89 (3 H, s, 18-CH$_3$), M+ (ammonia chemical ionization) 500 (M+NH$_3$).

2-Acetoxy-11α,17β-di(trimethylacetoxy)-estra-1,3,5(10)-triene (28).

A solution of the ketone (27) (40 mg. 0.83 mmol) and m-chloroperbenzoic acid (43 mg, 0.248 mmol) in dichloromethane (1 ml) was stirred for four days at room temperature in the dark. Addition of saturated sodium bicarbonate solution was followed by the usual working up procedure with methylene chloride to give a residue which was chromatographed on silica (2 g). Elution with ether-light petroleum (1:20) gave the product (28) (39 mg, 94%), m.p. 143°–146° C. (from ether-light petroleum), $\nu_{max}$ 1720 cm$^{-1}$ (C=O), δ (250 MHz) 7.10 (1 H, d, J 8 Hz, 4-proton), 6.86 (1 H, dd, J 8 and 2.5 Hz, 3-proton), 6.71 (1 H, d, J 2.5 Hz, 1-proton), 5.35 (1 H, dt, J 10.5 and 5 Hz, 11-proton), 4.65 (1 H, dd, J 8.5 and 7.5 Hz, 17-proton), 2.82 (2 H, t, J 7 Hz, 6-proton), 2.54 (1 H, t, J 10.5 Hz, 9-proton), 2.24 (3 H, s, CH$_3$CO), 1.21 (9 H, s, OBu$^t$), 1.19 (9 H, s, OBu$^t$), 0.89 (3 H, s, 18-CH$_3$), M+ (ammonia chemical ionization) 516 (M+NH$_3$).

Estra-1,3,5(10)-triene-2,11α,17β-triol (6D).

A solution of the triester (28) (150 mg, 0.30 mmol) in dry ether (3 ml) was treated with lithium aluminium hydride (46 mg, 1.41 mmol) at room temperature. After 5 min ethyl acetate (1 ml) and then dilute hydrochloric acid (1 ml) was added, and the mixture was worked up with ether in the usual manner. Chromatography of the crude product on silica (2 g) eluted with ethyl acetate gave the product (6D) (79 mg, 91%), m.p. 229°–232° C. (from acetone), $\nu_{max}$ (KBr disc) 3500 cm$^{-1}$ (OH), δ (MeOH) (250 MHz) 7.41 (1 H, dd, J 2.5 and 1 Hz, 1-proton), 7.39 (1 H, d, J 8 Hz, 4-proton), 6.86 (1 H, ddd, J 8, 2.5, and 1 Hz, 3-proton), 4.11 (1 H, dt, J 10.5 and 5 Hz, 11-proton), 3.67 (1 H, t, J 8.5 Hz, 17-proton), 3.68 (2 H, t, J 9 Hz, 6-protons), 2.21 (1 H, A part of ABX system, $J_{AX}$=5 Hz, $J_{AX}$=12 Hz), 2.20–1.20 (13 H, m), 0.74 (3 H, s, 18-CH$_3$), (Found: M+ 288.1719. C$_{18}$H$_{24}$O$_3$ requires M 288.1725).

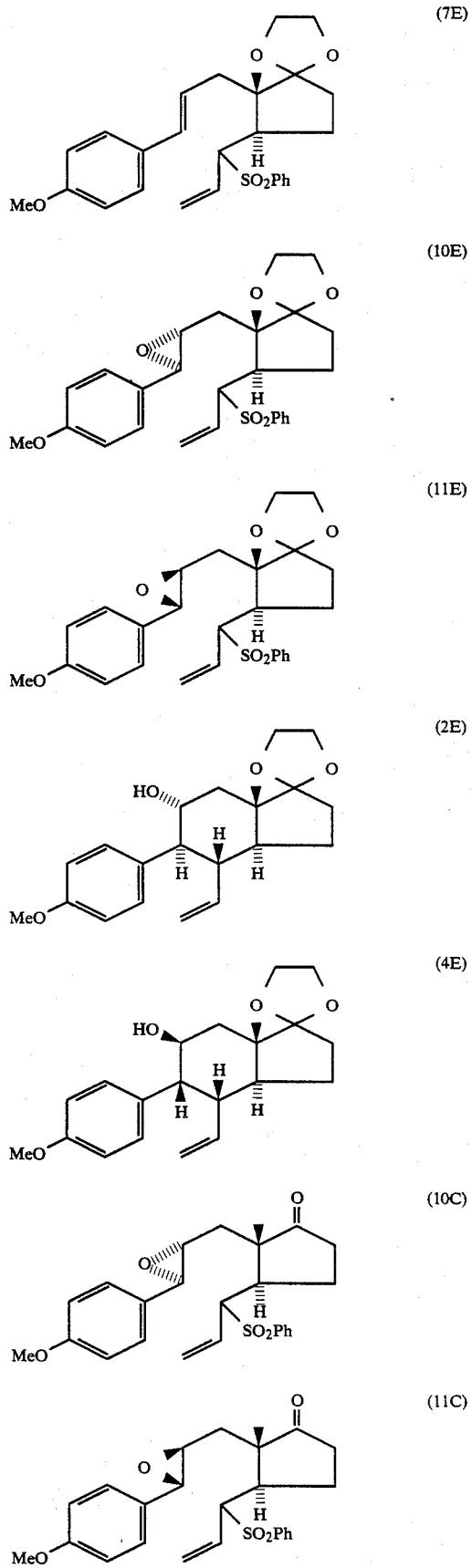

-continued
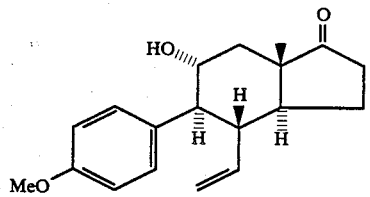
(2C)
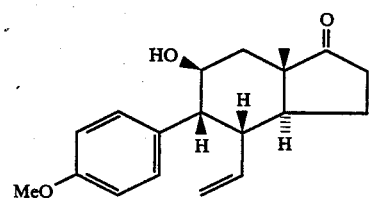
(4C)
I claim:
1. A compound having the formula
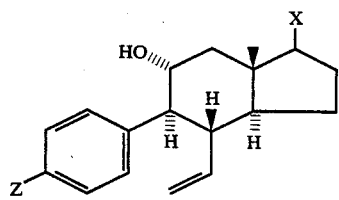
(2)
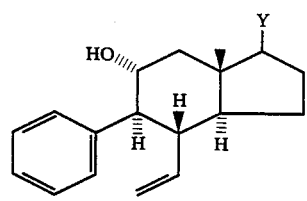
(2A)
-continued
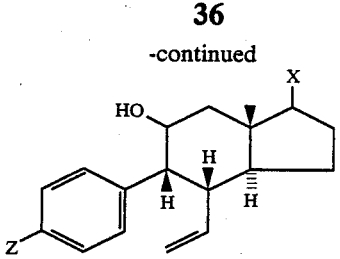
(4)
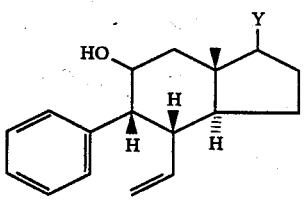
(4A)
where X represents =O,
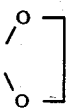
or beta orientated
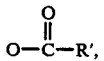
Y represents =O,
beta orientated
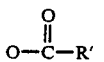
or beta orientated OH, Z represents alkoxy and R' represents alkyl.
* * * * *